(12) United States Patent
Walker et al.

(10) Patent No.: US 9,926,782 B2
(45) Date of Patent: Mar. 27, 2018

(54) AUTOMATED FLUID FRACTION SAMPLING SYSTEM

(71) Applicant: Chevron U.S.A. Inc., San Ramon, CA (US)

(72) Inventors: Dustin Luke Walker, Houston, TX (US); Robert Matthew Dean, Houston, TX (US)

(73) Assignee: CHEVRON U.S.A. INC., San Ramon, CA (US)

( * ) Notice: Subject to any disclaimer, the term of this patent is extended or adjusted under 35 U.S.C. 154(b) by 246 days.

(21) Appl. No.: 15/077,508

(22) Filed: Mar. 22, 2016

(65) Prior Publication Data

US 2016/0281500 A1 Sep. 29, 2016

Related U.S. Application Data

(60) Provisional application No. 62/138,562, filed on Mar. 26, 2015.

(51) Int. Cl.
| | |
|---|---|
| *E21B 49/08* | (2006.01) |
| *B01D 17/02* | (2006.01) |
| *B01D 19/00* | (2006.01) |
| *E21B 43/34* | (2006.01) |
| *G01N 1/10* | (2006.01) |
| *G01N 1/20* | (2006.01) |

(52) U.S. Cl.
CPC ........ *E21B 49/086* (2013.01); *B01D 17/0208* (2013.01); *B01D 19/0042* (2013.01); *B01D 19/0073* (2013.01); *E21B 43/34* (2013.01); *G01N 1/10* (2013.01); *G01N 2001/105* (2013.01); *G01N 2001/1031* (2013.01); *G01N 2001/2071* (2013.01)

(58) Field of Classification Search
CPC .................................................. E21B 49/086
See application file for complete search history.

(56) References Cited

U.S. PATENT DOCUMENTS

| | | | | |
|---|---|---|---|---|
| 6,032,539 A | * | 3/2000 | Liu ........................... | G01F 1/74 73/861.04 |
| 8,056,400 B2 | * | 11/2011 | Reintjes ................... | G01N 1/14 73/64.56 |
| 2015/0198039 A1 | * | 7/2015 | Marshall ............... | E21B 49/086 73/152.42 |
| 2015/0316527 A1 | * | 11/2015 | Stock ...................... | E21B 21/01 250/216 |

* cited by examiner

*Primary Examiner* — Shane Bomar

(57) ABSTRACT

Systems and methods for automated fluid sampling for tracer testing are described. In one aspect, an automated fluid sampling system includes a pressurized line, such as a production well or an injection well connectively and a fluid separation vessel receiving sample fluids therefrom. The fluid separation vessel includes a plunger and is configured for gravity-mediated phase separation of the sample fluids into a plurality of aqueous, organic and/or gas phase fluid fractions and includes pluralities of inlet and outlet ports for mediating flow of sample fluids therethrough. At least one purging fluid source, such as a gas or liquid, is used for driving the plunger. Sample fluid collection vessels receive phase-separated sample fluids from the fluid separation vessel. Pluralities of fluid lines and solenoid valves operatively link the pressurized line, purging fluid sources, sample fluid collection vessels, and disposal vessel to one another, whereby a controller selectively manages the automated flow of fluids through the various fluid lines.

71 Claims, 14 Drawing Sheets

AUTOMATED FLUID FRACTION SAMPLING SYSTEM

FIELD

The present disclosure relates generally to recovery and testing of fluid samples. More particularly, the present disclosure is directed to automated handling and sampling of fluids from a pressurized line source for tracer testing.

BACKGROUND

Tracers are frequently used in oil, water, and gas industries to track flow patterns and rates of the particular fluid to which it is introduced. Tracers are also used to study properties of the reservoir or aquifer in which the fluid resides. Tracers commonly are chemical compounds that have negligible effects on the producing fluid. In operation, tracers are injected into a reservoir or aquifer, and thereafter produced and sampled to measure for tracer concentration.

The present practice of sampling and measuring the concentration of a tracer produced from a reservoir or aquifer is rudimentary and involves a field operator manually collecting a sample, transporting the sample to a laboratory, filtering the sample, and finally measuring the sample for tracer concentration. In other embodiments, an automatic sampler is used to automatically extract a sample and seal it into a vial. However, an operator is still required to transport the vials to a laboratory facility where it is thereafter filtered and measured.

Sample contamination, operator burden, significant cost, and delay are frequently encountered problems with the current method for sampling and measurement of a tracer in a reservoir. Furthermore, failed tracer testing is due largely in part to problems created by poor sampling.

SUMMARY

In general terms, this disclosure is directed to an automated fluid sampling system, which may be used for detecting one or more tracers introduced in a reservoir for evaluation purposes.

In one aspect, the automated fluid sampling system includes a pressurized line connectively linked to a sample fluid source comprising sample fluids and a fluid separation vessel receiving the sample fluids from the pressurized line. The sample fluid source may be a production well or an injection well. The fluid separation vessel is configured for gravity-mediated phase separation of the sample fluids into a plurality of aqueous, organic and/or gas phase fluid fractions. The fluid separation vessel includes a plunger for collecting sample fluids into the fluid separation vessel and pluralities of inlet and outlet ports for mediating flow of sample fluids therethrough.

The system includes one purging fluid source containing a purging fluid for driving the plunger. The purging fluid may be a gas or a liquid. The system further includes one or more sample fluid collection vessels for receiving sample fluids from the fluid separation vessel; at least one disposal vessel for receiving sample fluids purged from the fluid separation vessel; pluralities of fluid lines and solenoid valves operatively linking the pressurized line, purging fluid sources, sample fluid collection vessel, and disposal vessel to one another; and a controller configured to manage the flow of fluids through the fluid sampling system in a predetermined manner. This arrangement of components may be employed for filling the fluid separation vessel with the sample fluids, collecting a phase separated fluid fraction into the sample fluid collection vessel, purging fluid remaining in the fluid separation vessel following collection of the phase separated fluid fraction, removing sample fluids purged from the fluid separation vessel into the disposal vessel, recycling a purging fluid into its corresponding fluid source, flushing one or more fluid lines downstream of the fluid separation vessel, or a combination thereof.

In certain preferred embodiments, the system includes a plurality of sample fluid collection vessels housed as an array in a sample box for collection of samples at multiple time points.

The system may further include a filtration system between the pressurized line and the fluid separation vessel for removing solids, salts, and other formations from the sample fluids.

The fluid lines include a sample fluid intake line, a sample fluid exit line, one or more collection vessel intake lines, one or more collection vessel exit lines, first and second sample fluid disposal lines, a purging fluid intake line, and at least one purging fluid exit line. In particular, the sample fluid intake line operatively links the pressurized line to the fluid separation vessel and the sample fluid exit line operatively links the fluid separation vessel to a first sample fluid disposal line, a collection vessel, a plurality of collection vessel intake lines, or a combination thereof.

Each collection vessel intake line is connectively linked to a collection vessel. The sample fluid exit line includes proximal and distal solenoid valves and a branchpoint therebetween. The first sample fluid disposal line originates at the branchpoint and is connectively linked to the second fluid disposal line or the disposal vessel. The second sample fluid disposal line operatively links the disposal vessel to the first purging fluid exit line, a collection vessel, a plurality of collection vessel exit lines, or a combination thereof, where each collection vessel exit line is connectively linked to a collection vessel. The purging fluid intake line operatively links the purging fluid source to the fluid separation vessel and a purging fluid exit line operatively links the fluid separation vessel to the second sample fluid disposal line or a vent to the atmosphere.

Each of the sample fluid intake line, the plurality of collection vessel intake lines, the plurality of collection vessel exit lines, the purging fluid intake line, the purging fluid exit line, and the first sample fluid disposal line includes a solenoid valve controlling flow of fluids therethrough. The controller is configured to open or close each of the solenoid valves in a predetermined manner.

Inlet and outlet ports are operatively positioned in the fluid separation vessel and appropriately connected to the fluid lines to facilitate selective removal of desired phase separated fluid fractions into one or more collection vessels. In particular, a sample fluid entry port is positioned for receiving sample fluids from the sample source via the pressurized line. A sample fluid exit port is positioned for removing a selected phase separated fluid fraction from the fluid separation vessel via the sample fluid exit line. A purging fluid entry port is positioned for receiving a purging fluid from the purging fluid source via the purging fluid intake line to facilitate collection of the phase separated fluid fraction, purging of sample fluids remaining in the fluid separation vessel following collection of the phase separated fluid fraction, or both. A purging fluid exit port is positioned for removing a purging fluid or sample fluids remaining in the fluid separation vessel following removal of the phase separated fluid fraction from the fluid separation vessel via the purging fluid exit line, and collection of a phase separated fluid fraction into a collection vessel.

In one embodiment, the system includes first and second purging fluids sources, first and second purging fluids, where the fluid separation vessel includes first and second purging entry ports and first and second purging fluid ports. In this arrangement, the second purging fluid is recycled back to the second purging source via a second purging fluid exit line following collection of the phase separated fluid fraction.

In some embodiments, the pluralities of inlet ports, outlet ports, and fluid lines are operatively positioned for collecting one or more aqueous phase fluid fraction samples in one or more sample fluid collection vessels.

In other embodiments, the pluralities of inlet ports, outlet ports, and fluid lines are operatively positioned for collecting one or more gas phase fluid fraction samples in one or more sample fluid collection vessels.

In yet other embodiments, the pluralities of inlet ports, outlet ports, and fluid lines are operatively positioned for collecting one or more organic phase fluid fraction samples in one or more sample fluid collection vessels.

In another aspect, method for obtaining sample fluids from a sample fluid source includes the steps of:

(a) providing an automated fluid sampling system in accordance with the present application;

(b) filling the fluid separation vessel with sample fluids from the sample fluid source via the pressurized line;

(c) allowing a sufficient period of time for gravity-mediated phase separation of the sample fluids into at least two phase separated fluid fractions; and (d) collecting a selected phase separated fluid fraction in a sample fluid collection vessel.

The method may further repeating steps (b)-(d) to collect a phase separated fluid fraction in each of the plurality of sample fluid collection vessels.

Collection of phase separated fluid fraction samples in one or more sample fluid collection vessels may be carried out by opening or closing solenoid valves operatively linked to the various fluid lines in a predetermined manner. This may entail opening or closing the solenoid valves in a manner dependent on time, sample fluid source, fluid pressure, fluid flow rate or a combination thereof. Depending on the arrangement of fluid lines and ports in the fluid separation vessel, the solenoid valves may be appropriately opened or closed to facilitate selective collection of one or more aqueous phase fluid fraction samples, one or more gas phase fluid fraction samples, one or more organic phase fluid fraction samples, or a combination thereof.

In certain embodiments, the step of collecting the phase separated fluid fraction in a collection vessel is coincident with introduction of a purging fluid into the fluid separation vessel.

In some embodiments, the step of collecting the phase separated fluid fraction in a collection vessel involves introducing a purging fluid into the fluid separation vessel so as to vertically displace the plunger and fluids contained on the opposite side of the plunger.

In other embodiments, the step of collecting the phase separated fluid fraction in a collection vessel includes the step of introducing a purging fluid directly behind sample fluids on the same side of the plunger so as to drive a phase separated fluid fraction out of the fluid separation vessel toward a sample fluid collection vessel.

In other embodiments, the step of collecting the phase separated fluid fraction in a collection vessel includes introducing a purging fluid into the fluid separation vessel so as to displace the plunger in the fluid separation vessel and drive a phase separated fluid fraction on the other side of the plunger out of the fluid separation vessel toward a sample fluid collection vessel.

In other embodiments, the step of collecting the phase separated fluid fraction in a collection vessel is coincident with removal of a purging fluid within the fluid separation vessel.

In some embodiments, the method may further includes the step of introducing a purging fluid through the fluid separation vessel to flush out a fluid line downstream of the fluid separation vessel, recycling a purging fluid from the fluid separation vessel back to its corresponding purging fluid source, or both.

In other embodiments, the method may further include the step of removing solids, salts, and/or other formations received from the pressurized line by passing the sample fluid through a filtration system.

In some embodiments, the automated fluid sampling system is located in an oil well field and the method further includes the step of introducing a tracer into an injection well or production well located in the oil well field. Tracers may be introduced in a plurality of injection wells, production wells, or a combination thereof, where the injection wells and production wells are located in the oil well field.

In other embodiments, the automated fluid sampling system is located in a gas well field and the method further comprises the step of introducing a tracer into an injection well or production well located in the gas well field. Tracers may be introduced in a plurality of injection wells, production wells, or a combination thereof, where the injection wells and production wells are located in the gas well field.

In a further aspect, a method for assembling an automated fluid sampling system 10 includes the steps of operatively linking:

(a) a pressurized line to a plunger equipped fluid separation vessel by a sample fluid intake line, the pressurized line being operatively linked to a sample fluid source comprising sample fluids;

(b) the plunger equipped fluid separation vessel to a sample fluid exit line, a purging fluid intake line, and a purging fluid exit line;

(c) the sample fluid exit line to a first sample fluid disposal line and a plurality of collection vessel intake lines;

(d) a second sample fluid disposal line to a disposal vessel;

(e) the first sample fluid disposal line to a disposal vessel or the second sample fluid disposal line;

(f) each of the plurality collection vessel intake lines to a collection vessel;

(g) each of the collection vessels to one of a plurality of collection vessel exit lines;

(h) each of the plurality of collection vessel exit lines to the second sample fluid disposal line;

(i) a solenoid valve to each of the sample fluid intake line, the sample fluid exit line, the first sample fluid disposal line, the purging fluid intake line, the purging fluid exit line, and each of the pluralities of collection vessel intake lines and collection vessel exit lines, each solenoid valve being configured to selectively control fluid flow therethrough; and (j) a controller to the solenoid valves so that each of the solenoid valves can be selectively opened or closed in a predetermined manner.

DETAILED DESCRIPTION

Figure 1:
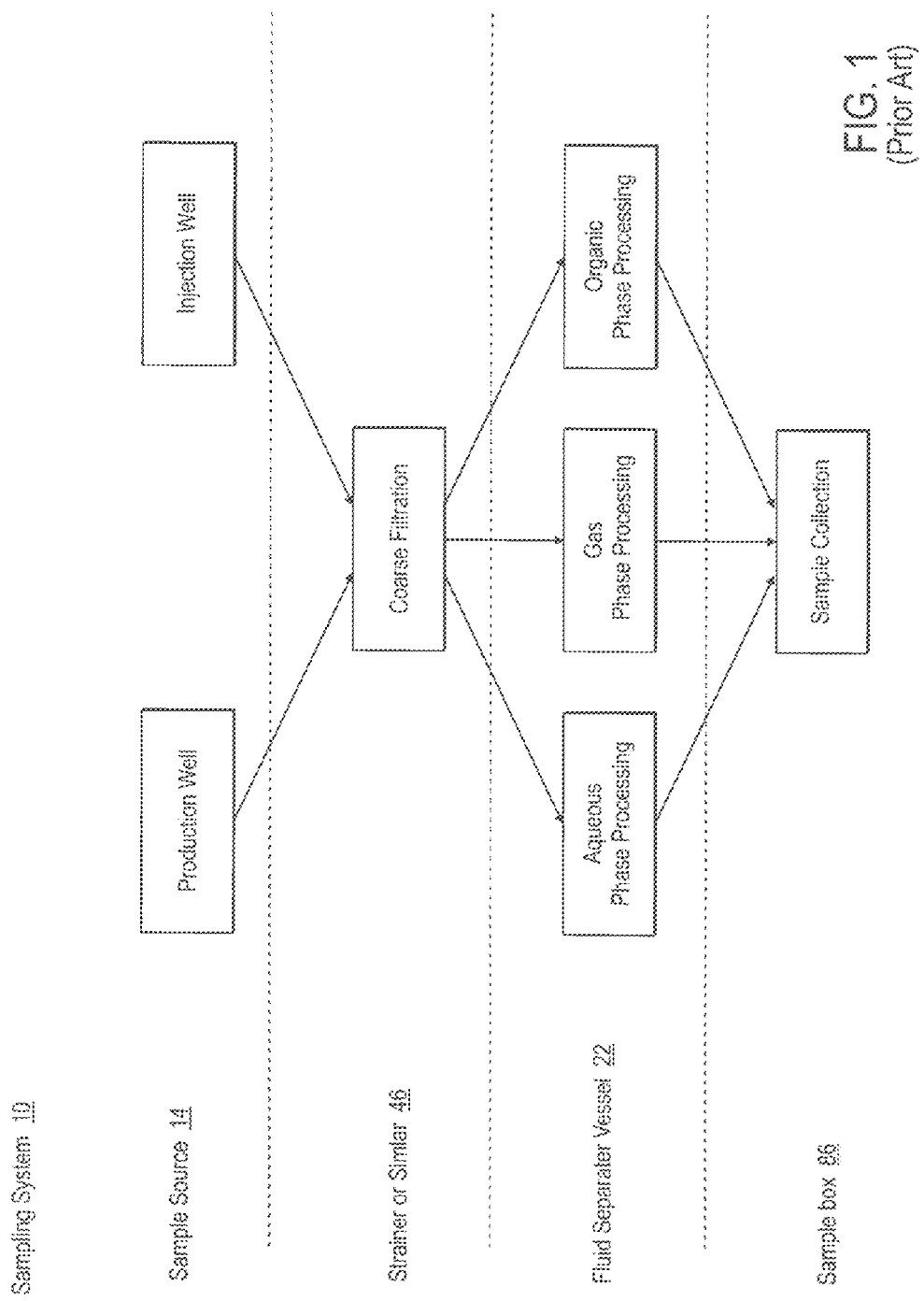
FIG. 1 is a flow chart depicting a general scheme for collection of phase separated fluid fractions from a fluid source.

Various embodiments will be described in detail with reference to the drawings, where like reference numerals represent like parts and assemblies throughout the several views. Reference to various embodiments does not limit the scope of the claims attached hereto. Additionally, any examples set forth in this specification are not intended to be limiting and merely set forth some of the many possible embodiments for the appended claims.

FIG. 1 is a flow chart depicting a general scheme for collecting phase separated fluid fractions from a sample fluid source using an automated fluid sampling system according to one embodiment. Briefly, sample fluids are drawn from a pressurized line operatively linked to a sample fluid source, such as a production well or injection well in an oil well field or gas well field. The sample fluids may be subjected to coarse filtration system using e.g., a strainer or functionally analogous system prior to passage through a plunger equipped fluid separation vessel. The fluid separation vessel is configured for gravity-mediated phase separation of the sample fluids into a combination of at least two aqueous, organic, and gas phase fluid fractions. The fluid separation vessel includes a plunger for collecting sample fluids into the fluid separation vessel and purging fluids therefrom. The fluid separation vessel further includes pluralities of inlet and outlet ports for mediating flow of sample fluids therethrough. In particular, selected fluid fractions are withdrawn from the fluid separation vessel into one or more sample fluid collection vessels, preferably arranged in a sampling array.

Figure 2:
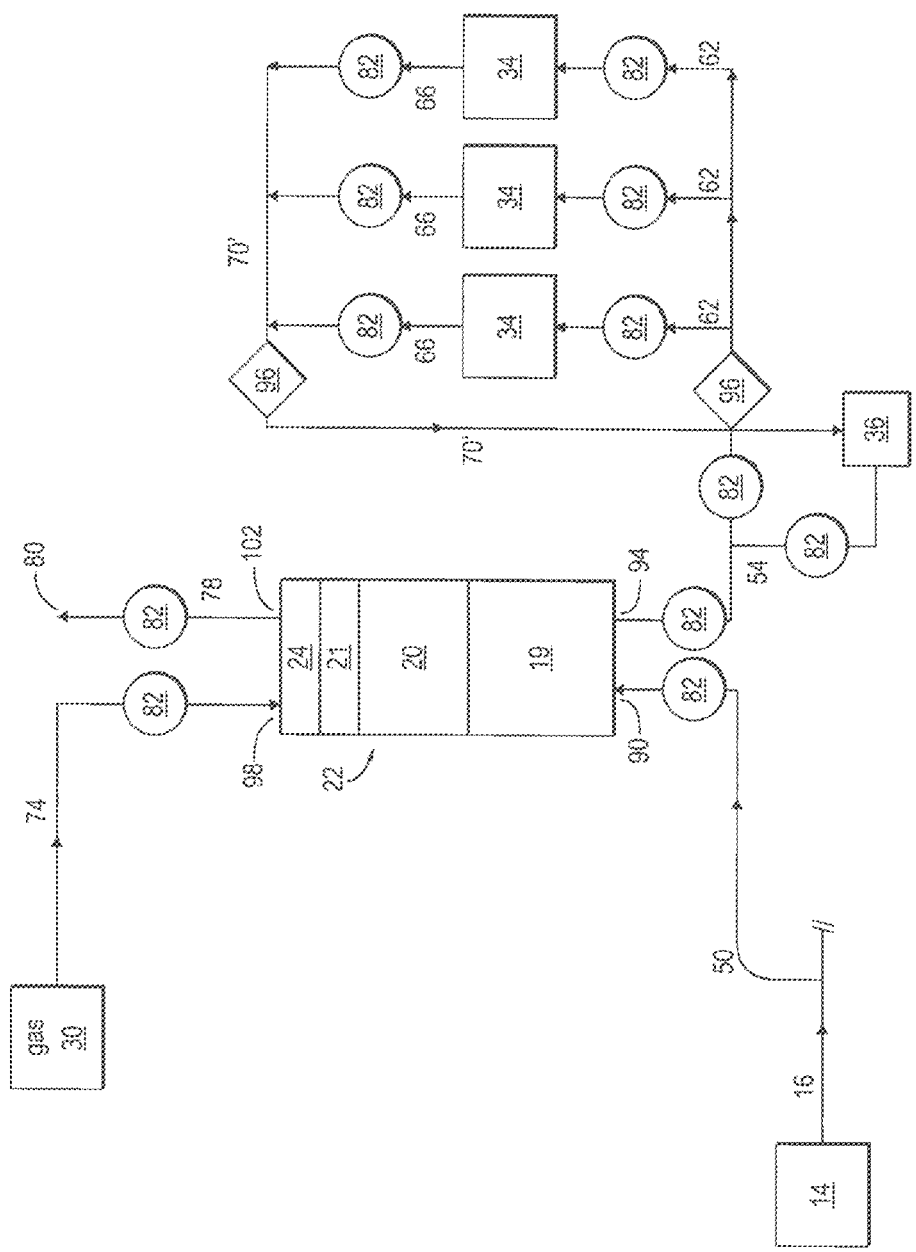
FIG. 2 is a schematic diagram of an automated aqueous phase fluid fraction collection system according to one embodiment.

FIG. 2 is schematic depiction of an automated aqueous phase sampling system 10 according to one embodiment. In this embodiment, the aqueous phase sampling system 10 includes a pressurized line 16 carrying sample fluids 12 from a sample fluid source 14 and a plunger fluid separation vessel 22 receiving the sample fluids 12 from the pressurized line 16. The sample fluid source 14 may be a production well or injection well. The system 10 may be configured to receive sample fluids 12 from a plurality of production wells and/or injection wells located in an oil well field, gas well field or combination thereof. In certain preferred embodiments, the system 10 includes a filtration system 46 between the pressurized line 16 and the fluid separation vessel 22 for removing solids, salts, and other formations from the sample fluids 12.

The fluid separation vessel 22 is configured for gravity-mediated phase separation of the sample fluids 12 into aqueous phase 19, organic phase 20, gas phase 21 fluid fractions or combinations thereof. The fluid separation vessel 22 includes a plunger 24 for collecting sample fluids 12 in the fluid separation vessel 22 and for purging fluids from the fluid separation vessel 22. Pluralities of inlet ports 25 and outlet ports 26 may be disposed in top, bottom or side portions of the fluid separation vessel 22 for mediating flow of sample fluids 12 therethrough;

A purging fluid source 30 contains a purging fluid 32 for actuating the plunger 24 so as to drive sample fluids out of the fluid separation vessel 22. The purging fluid 32 can be a gas or liquid. One or more sample fluid collection vessels 24 are configured to selectively receive phase separated fluid fractions, e.g., 19, 20, 21 from the fluid separation vessel 22. Although FIG. 2 depicts a system 10 for collecting aqueous phase fluid fractions 19, the system 10 can be modified for collection of gas phase 21 and organic phase 20 fluid fractions as further illustrated in the Figures below. A disposal vessel 36 receives sample fluids 12 purged from the fluid separation vessel 22.

To selectively manage the flow of fluids, the system 10 includes a plurality of fluid lines and a plurality of solenoid valves 82 operatively linking the pressurized line 16, fluid separation vessel 22, purging fluid source(s) 30, sample fluid collection vessel(s) 34, and disposal vessel(s) 36 to one another for filling the fluid separation vessel 22 with the sample fluids 12. A controller 42 is configured to manage the flow of fluids 12 through the fluid sampling system 10 in a predetermined manner. This is achieved by selectively opening and closing the solenoid valves 82 present in the various fluid lines according to a predetermined sequence of operation steps.

In accordance with the design of the systems 10 described herein, the automated sample collection system 10 may be configured to automatically collect a particular phase separated fluid fraction sample 19, 20 or 21 into a sample fluid collection vessel 34, purge fluid 32 remaining in the fluid separation vessel 22 following collection of the phase separated fluid fraction sample 19, 20, 21, discard sample fluids 12 purged from the fluid separation vessel 22 into the disposal vessel 36, recycle purging fluids 32 into their corresponding fluid source 30, and flush out fluid lines downstream of the fluid separation vessel 22.

To accomplish these various tasks, the system 10 includes a sample fluid intake line 50, a sample fluid exit line 54, a sample fluid disposal line 70, a purging fluid intake line 74, and a purging fluid exit line 78. The sample fluid intake line 50 operatively links the pressurized line 16 to the fluid separation vessel 22. The sample fluid exit line 54 operatively links the fluid separation vessel 22 to a collection vessel 34 or a plurality of collection vessel intake lines 62, each connectively linked to a corresponding collection vessel 34. A sample fluid disposal line 70 operatively links the disposal vessel 34 to the sample fluid exit line 54, a plurality of collection vessel exit lines 66, or both. A first sample fluid disposal line or bypass line 70 connectively links the sample fluid exit line 54 to a second sample fluid disposal line connectively linking a collection vessel 34 or plurality of collection vessel exit lines 66 to the disposal vessel 36. As shown in FIG. 2, the first sample fluid disposal line 70 extends from a second branchpoint 130 in the sample fluid exit line 54. When using the embodiment in FIG. 2 to collect an aqueous phase 19 fluid fraction, the first sample fluid disposal line 70 is used as a bypass line for removing organic phase 20 and gas phase 21 fluid fractions as the purging fluid 32 from the purging fluid source 30 is introduced through the top of the fluid separation vessel 22.

A purging fluid intake line 74 operatively links a purging fluid source 30 to the fluid separation vessel. A purging fluid exit line 78 operatively links the fluid separation vessel 22 to the second sample fluid disposal line 70' or vent to the atmosphere 80. Each of the sample fluid intake line 50, sample fluid exit line 54, sample fluid exit line 70, collection vessel intake lines 62, collection vessel exit lines 66, purging fluid intake line 74, and purging fluid exit line 78 comprises a solenoid valve 82 controlling flow of sample fluids 12 therethrough. A controller 42 is configured to open or close each of the plurality of solenoid valves 82 in a predetermined manner. Whereas an open solenoid valve 82 allows flow through its corresponding fluid line, a closed solenoid valve 82 prevents flow through its corresponding fluid line. The solenoid valves 82 may be opened or closed in a predetermined manner. The predetermined manner by which the solenoid valves are opened or closed may be dependent on time, sample fluid source, fluid pressure, fluid flow rate or a combination thereof.

Figure 3A:
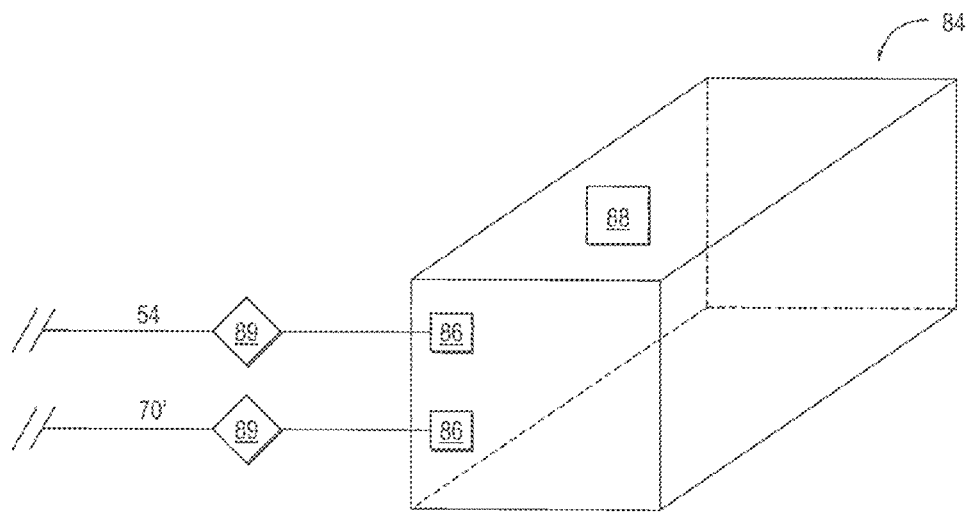
FIGS. 3A and 3B depict various aspects of an exemplary sample box containing an array of collection vessels.
Figure 3B:
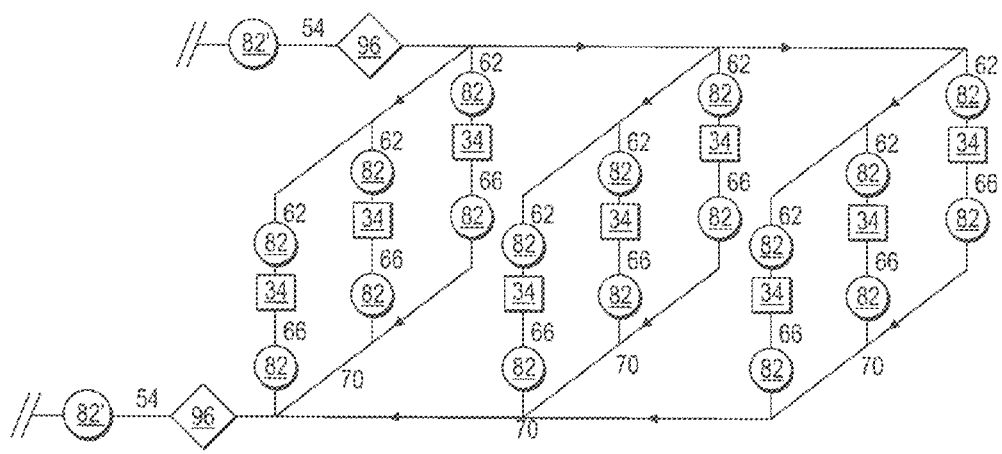

Preferably, the system 10 includes a plurality of sample fluid collection vessels 34 housed as an array in a sample box 84 as shown in FIGS. 3A and 3B. In one embodiment depicted in FIG. 3A, the sample box 84 includes a controller hookup 88, a sample box entry port 86 and a sample box exit port 87. The array may include at least 2, at least 3, at least 4, at least 5, at least 6, at least 7, at least 8, at least 10, at least 12, at least 14, at least 18, at least 20, at least 24, at least 28, at least 48, at least 50, at least 64, or at least 100 or more sample collection fluid collection vessels 34.

The sample fluid exit line 54 extends into the sample box 84 through the sample box entry port 86 and includes a disconnect 96 for disengaging the sample fluid exit line 54 from the sample box 84 at a position downstream of the second (or distal) solenoid valve 82' near the sample box entry port 86 (FIG. 3B). The second sample fluid disposal line 70' extends out from the sample box 86 through the sample box exit port 87 and includes a disconnect 96 for disengaging the second sample fluid disposal line 70 from the sample box 84 near the sample box exit port 87.

In certain embodiments, the system 10 may further include a rack of supply magazine operated with an actuator for moving a disengaged sample box 84 with filled sample fluid collection vessels 34 along a conveyor so that a new sample box may be transported to the sample collection area and/or a filled sample box may be transported away from the sample collection area to a suitable holding place for collection by an operator.

The system 10 includes pluralities of inlet ports and outlet ports operatively positioned in top, bottom, or side portions of the fluid separation vessel 22, each of the ports being operatively connected to a particular fluid line. The system 10 in FIG. 2 includes a sample fluid entry port 90 in the bottom of the fluid separation vessel 22 for receiving sample fluids 12 from the pressurized line 16 and a sample fluid exit port 94 in the bottom of the fluid separation vessel 22 for removal of the aqueous fraction 19 via the sample fluid exit line 54. A purging fluid entry port 98 disposed in a top portion of the fluid separation vessel receives a purging fluid 32 from the purging fluid source 30 via the purging fluid intake line 74 to facilitate collection of the phase separated fluid fraction 18, purging of sample fluids 12 remaining in the fluid separation vessel 22 following collection of the phase separated fluid fraction 18, or both, as further described below. The purging fluid 32 and/or or sample fluids remaining in the fluid separation vessel 22 following collection of the phase separated fluid fraction may be removed via a purging fluid exit port 102 in the top of the fluid separation vessel operatively linked to a purging fluid exit line 78. In FIG. 2, the purging fluid 32 is a gas and the purging fluid exit line 78 includes a vent 80 for discarding the gas into the atmosphere. Gases for use as purging fluids are preferably compressed gases containing nitrogen, and combinations thereof.

In other embodiments, the purging fluid 32 may be a liquid which may be collected in a disposal vessel 36 or recycled through the purging fluid source 30.

To collect a phase separated fluid fraction from the automated sample collection system 10, the fluid separation vessel 22 is first filled with sample fluids from the sample fluid source 14. A sufficient period of time is allowed for gravity-mediated phase separation of the collected sample fluids 12 in the fluid separation vessel 22 into one or more phase separated fluid fractions 19, 20 and/or 21. Following phase separation of the fluids, a selected phase separated fluid fraction 19, 20 or 21 is collected into a designated sample fluid collection vessel 34. This is achieved by flowing a purging fluid 32 into the fluid separation vessel 22 to drive the plunger 24 upward or downward so as to expel fluids from selected sample fluid fractions 19, 20 or 21 into a designated sample fluid collection vessel 34 or into a sample fluid disposal vessel 36.

Following collection or removal of the selected sample fluid fraction 19, 20 or 21, purging fluids 32 and other sample fluids remaining in the fluid separation vessel 22 are removed. In certain embodiments, purging fluids 32 may be introduced into one or more fluid lines downstream of the fluid separation vessel 22 to flush out fluids remaining in the lines.

To collect a series of phase separated fluid fractions in a predetermined time sequence, a sample box 84 housing an array of collection vessels 34 may be employed as further shown in FIGS. 3A and 3B, whereby the above series of steps are repeated for collection of phase separated fluid fractions into each successive collection vessel 34 by selectively opening and closing appropriate solenoid valves 82 linked to the various collection vessel intake lines 62. The array of collections vessels 34 may be housed in the sample box 84 as a "closed system". As used herein, a "closed system" refers to a fluid sample recovery system that can be maintained during and after the course of sampling in a substantially entirely or entirely closed system without exposure to the atmosphere or environment, thereby diminishing the risk of compromising the integrity of the collected samples by liquid or vapor leakage from the collection vessels before or after disconnection from the automated fluid sampling system 10 so as to retain and preserve substantially all or entirely all of the collected sample fluids in their originally collected state.

Figure 4:
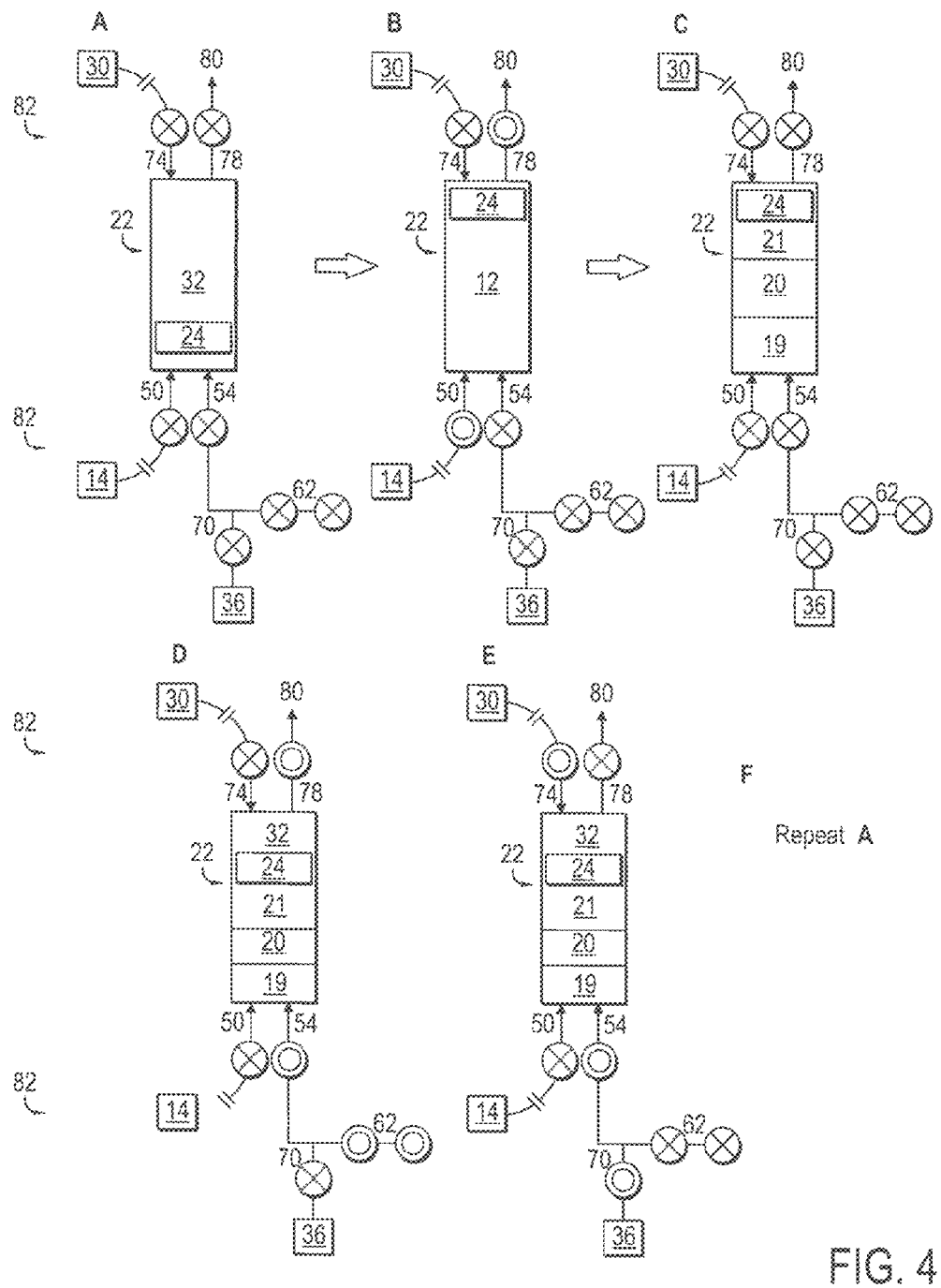
FIG. 4 depicts the sequence of steps associated with collection of an aqueous phase fluid fraction from the system depicted in FIG. 2.

To initiate an aqueous phase sample collection sequence collect using the system 10 depicted in FIG. 2, the plunger 24 is initially positioned at the bottom of the fluid separation vessel 22, which is filled above the plunger 24 with a purging fluid 32, such as compressed gas (Step A of FIG. 4). At the start of the collection sequence, the controller 42 has closed the solenoid valves 82 in each of the purging fluid intake line 74, purging fluid exit line 78, sample fluid intake line 50 and sample fluid exit line 54 so as to prevent flow of fluids therethrough.

Then, as shown in Step B of FIG. 4, at a predetermined time, the controller 42 selectively opens the sample fluid intake line 50 and the sample fluid exit line 78 so that the sample fluids from the sample fluid source 14 flow through the sample fluid entry port 90 and into the fluid separation vessel 22, driving the purging fluids 32 on the opposite side of the plunger 24 to flow out of the fluid separation vessel 22 through the purging fluid exit line 78. Although the purging fluid exit line 78 depicted in FIG. 2 contains a vent 80 where the purging fluid 32 is a gas, in alternative embodiments, the purging fluid 32 may be a liquid. In that case, the purging fluid exit line 78 may be operatively linked to a disposal vessel 36 or it may be operatively linked to a second purging fluid exit line for recycling the liquid 32 back to the liquid purging fluid source 30.

Upon filling the fluid separation vessel 22 with the sample fluids 12, the solenoid valves 82 in all of the fluid lines connected (or indirectly connected) to the fluid separation vessel 22, e.g., 50, 54, 74 and 78 are closed for a period of time sufficient for phase separation of the sample fluids 12 into aqueous phase 19, organic phase 20 and/or gas phase 21 fluid fractions as shown in Step C of FIG. 4. Then, as shown in Step D of FIG. 4, each of the purging fluid intake line 74, both solenoid valves 82, 82' in the sample fluid exit line 54, and a predetermined collection vessel intake line 62 is opened so that as purging fluid 32 enters the fluid separation vessel 22 via the purging fluid intake line 74, at least a portion of the aqueous phase fluid fraction 19 is removed from the fluid separation vessel 22 via the sample fluid exit line 54 into the collection vessel 34.

Upon collection of the aqueous phase fluid fraction 19, the collection vessel intake line is 62 closed and the first sample fluid disposal line 70 is opened so that the remainder of the sample fluids can flow out of the fluid separation vessel 22 into the sample disposal vessel 36 as the fluid separation vessel is filled with the purging fluid 32 (As show in Step E of FIG. 4). Once the fluid separation vessel 22 is filled with the purging fluid 32, each of the purging fluid intake line 74, purging fluid exit line 78, sample fluid intake line 50 and sample fluid exit line 54 is closed to prevent flow of fluids into and out of the fluid separation vessel 22 until the next fluid fraction 19 is collected in accordance with the above described steps.

FIGS. 5-8 depict alternative aqueous phase sampling system 10 embodiments employing two purging fluid sources 30, 30', two purging fluid intake line 74, 74' associated therewith, and two purging fluid exit lines 54, 78.

Figure 5:
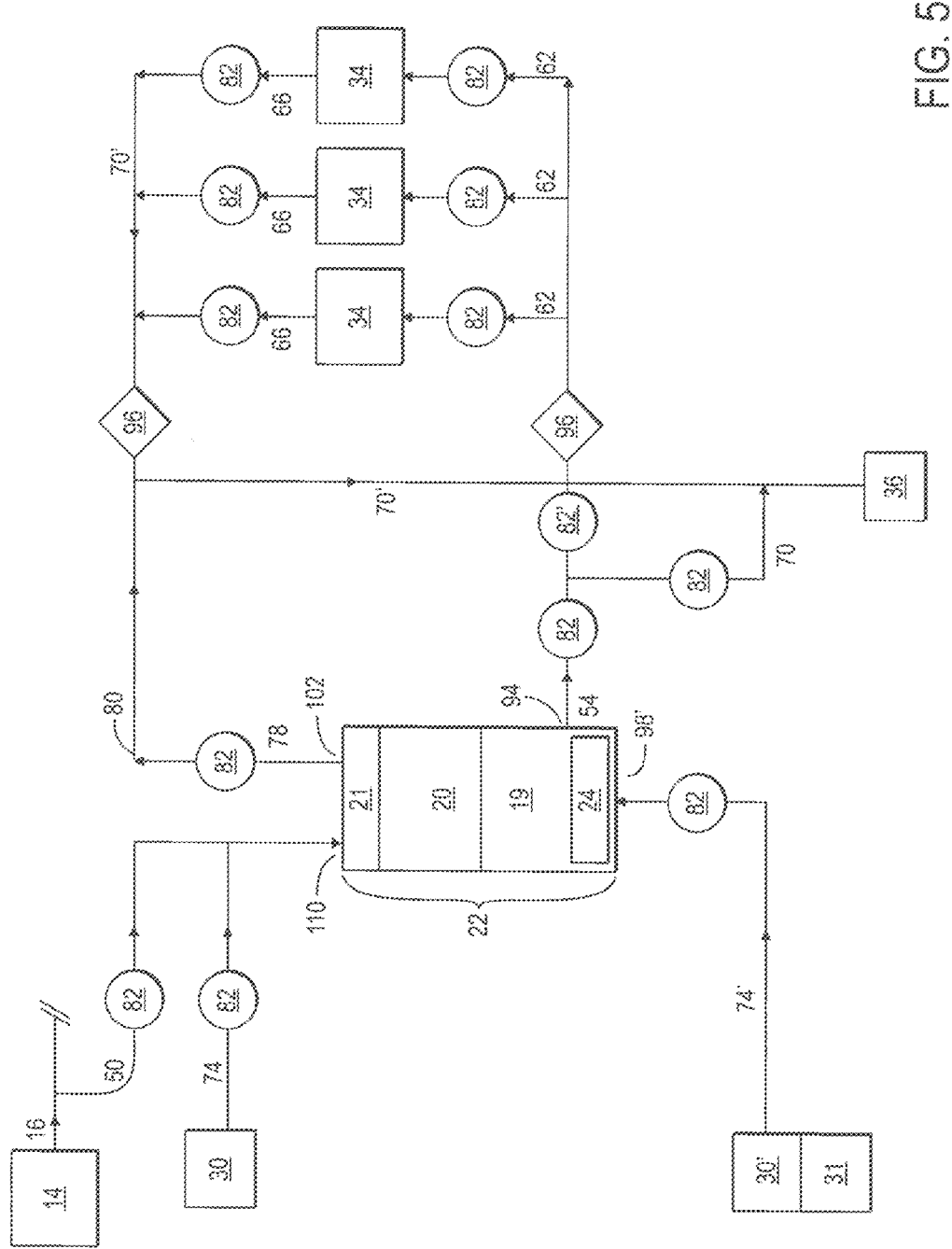
FIG. 5 is a schematic diagram of an automated aqueous phase fluid fraction collection system according to a second embodiment.

FIG. 5 depicts a system 10 that includes first and second purging fluid sources 30, 30', first and second purging fluids 32, 32', first and second purging fluid intake lines 74, 74' and a single purging fluid exit line 78, and first and second sample fluid disposal lines 70, 70'. Each of the first and second purging fluid intake lines 74, 74', the purging fluid exit line 78 and the first sample fluid disposal line 70 comprises a solenoid valve operatively linked to the controller for selectively managing flow of sample fluids therethrough in a predetermined manner. The sample fluid exit line 54 includes a proximal solenoid valve 82 upstream of a branchpoint 130 from which the first sample fluid disposal line 70 originates, and a distal solenoid valve 82' upstream of a disconnect 96 proximal to the collection vessel intake lines 62.

In this embodiment, the first purging fluid intake line 74 connectively links the first purging fluid source 30 to the fluid separation vessel 22 via a first purging fluid entry port 110 disposed in the top of the fluid separation vessel 22. As such, the first purging fluid entry port 110 also connectively links the sample fluid entry line 50 to the fluid separation vessel 22. In this configuration, the first purging fluid entry port 110 receives the first purging fluid 32 from the first purging fluid source 30 so as to drive out at least a portion of the aqueous phase fluid fraction 19 through a sample fluid exit port 94 disposed in the side of the fluid separation vessel 22 via the sample fluid exit line 54.

The sample fluid exit line 54 connectively links a sample fluid exit port 94 disposed in the side of the fluid separation vessel 22 to the collection vessel. In this case, the sample fluid exit port 94 is positioned just above the plunger 24 when the plunger 24 is fully displaced to the bottom 28 of the fluid separation vessel 22. The first sample disposal line 70 extends from a branchpoint 130 in the sample fluid exit line 54 for removing the second purging fluid 32' below the plunger 24 of the fluid separation vessel 22 as the sample fluids 12 are introduced into the fluid separation vessel. Although the first sample disposal line 70 is depicted in FIG. 5 as connectively joining the sample fluid exit line 54 to the second sample fluid disposal line 70', alternatively, it may be directly linked to the disposal vessel 36 depicted in FIG. 5 or even a second disposal vessel 36 (not shown).

The second purging fluid intake line 74' connectively links the second purging fluid source 30' to the fluid separation vessel 22 via a second purging fluid entry port 98' disposed in the bottom of the fluid separation vessel 22. The second purging fluid entry port 98' is positioned for receiving the second purging fluid 32' from the second purging fluid source 30' so as to drive out fluids remaining above the plunger 24 through the purging fluid exit port 102 via the purging fluid exit line 78 following removal of the aqueous phase fluid fraction 19. The purging fluid exit line 78 is further linked to the second sample disposal line 70' for removing fluids displaced through the top of the fluid separation vessel 22 following introduction of the second purging fluid 32' at the bottom of the fluid separation vessel 22.

Figure 6:
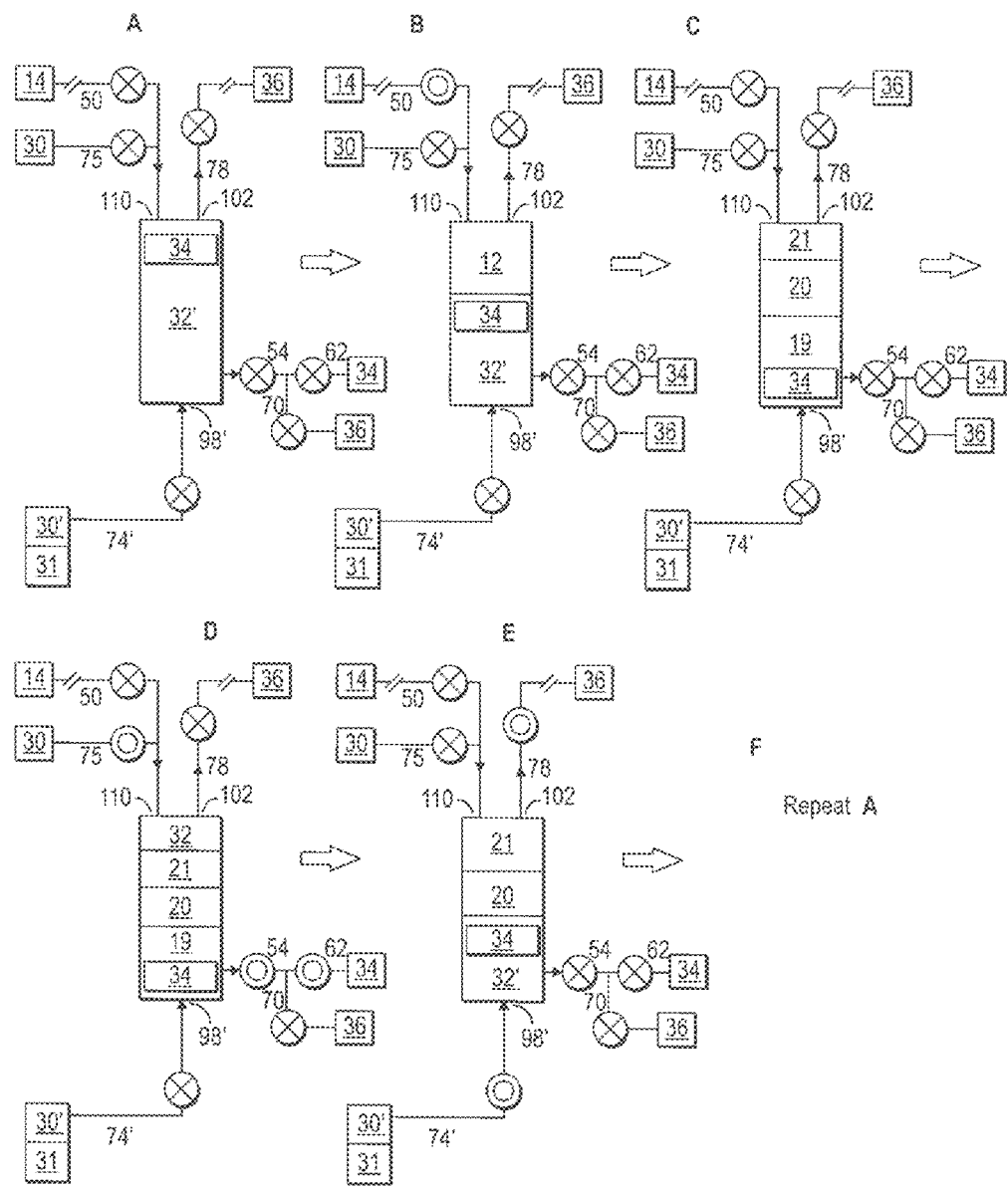
FIG. 6 depicts the sequence of steps associated with collection of an aqueous phase fluid fraction from the system depicted in FIG. 5.

To initiate an aqueous phase sample collection sequence using the system 10 depicted in FIG. 5, the plunger 24 is initially positioned near the top of the fluid separation vessel 22, above a filled column of the second purging fluid 32' (Step A of FIG. 6). At the start of a collection sequence, the controller 42 has closed solenoid valves 82 in each of the first and second purging fluid intake lines 74, 74', the purging fluid exit line 78, the sample fluid intake line 50, the sample fluid exit line 54, and the first sample fluid disposal line 70 so as to prevent flow of fluids there through.

Then, as shown in Step B of FIG. 6, at a predetermined time, the controller 42 selectively opens the solenoid valve 82 in the sample fluid intake line 50, the proximal solenoid valve 82 in the sample fluid exit line 54, and the solenoid valve 82 in the first sample fluid disposal line 70 so that the sample fluids 12 from the sample fluid source 14 can flow through the sample fluid entry port 110 and into the fluid separation vessel 22, driving the second purging fluid 32' on the opposite side of the plunger 24 to flow out of the fluid separation vessel 22, through the proximal portion of the sample fluid exit line 54, through the first sample fluid disposal line 70 and into the sample fluid disposal vessel 36. Where the second purging fluid 32' is a gas, the proximal solenoid valve 82 in the sample fluid collection line 54 is closed and the bottom of the fluid separation vessel 22 is additionally provided with a second purging fluid exit port 102' (not shown) with a vent 80 for expelling the gas.

Once the fluid separation vessel 22 is filled with the sample fluids 12 and the plunger 24 is displaced to the bottom of the fluid separation vessel 22, the solenoid valves 82 in all of the fluid lines directly connected to the fluid separation vessel 22, e.g., 50, 54, 70, 74, 74', 78 are closed for a period of time sufficient for phase separation of the sample fluids 12 into aqueous phase 19, organic phase 20 and/or gas phase 21 fluid fractions as shown in Step C of FIG. 6.

Then, as shown in Step D of FIG. 6, the solenoid valve 82 in the first purging fluid intake line 74 is opened, the proximal and distal solenoid valves 82, 82' in the sample fluid exit line 54 are opened, and a predetermined collection vessel intake line 62 is opened so that as the first purging fluid 32 enters the fluid separation vessel 22 via the first purging fluid intake line 74, at least a portion of the aqueous phase fluid fraction 19 is removed from the fluid separation vessel 22 via the sample fluid exit line 54 and the collection vessel intake line 62, into a predetermined collection vessel 34.

Upon collection of the aqueous phase fluid fraction 19, the solenoid valves 82 in each of the first purging fluid intake line 74, the sample fluid exit line 54, and the previously opened collection vessel intake line 62 are closed, and each of the second purging fluid intake line 74' and first purging fluid exit line 78 is opened so that sample fluids remaining in the fluid separation vessel 22 above the plunger 24 are diverted to the disposal vessel 36 via the first purging fluid exit line 78 and the second sample fluid disposal line 70' (As Shown in Step E of FIG. 6). Once the second purging fluid 32' drives out all of the remaining fluids above the plunger 24 and displaces the plunger 24 to the top of the fluid separation vessel 22, all of the solenoid valves 82 are closed until the next sample collection sequence is initiated.

Figure 7:
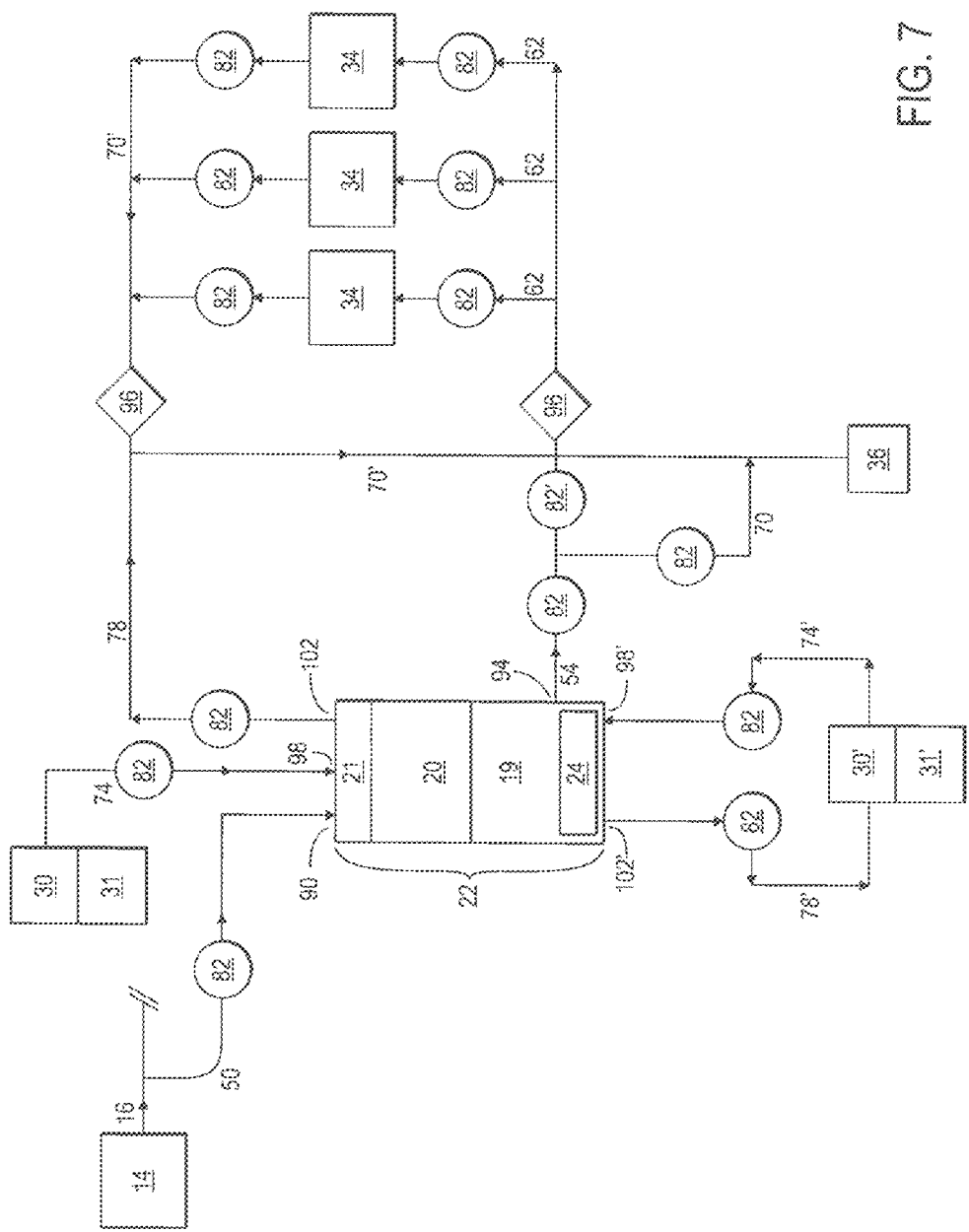
FIG. 7 is a schematic diagram of an automated aqueous phase fluid fraction collection system according to a third embodiment.

FIG. 7 depicts a system 10 that includes first and second purging fluid sources 30, 30' for introducing first and second purging fluids 32, 32' into the fluid separation vessel 22 via first and second purging fluid intake lines 74, 74' operatively linked to first and second purging fluid entry ports 98, 98'. The system 10 further includes two purging fluid exit lines 78, 78', including a second purging fluid exit line 78' for recycling the second purging fluid 32' used to purge sample fluids 12 remaining in the fluid separation vessel 22, recycling them back into the second purging fluid source 30' following collection of the aqueous phase fluid fraction 19.

In this configuration, the first purging fluid 32 and/or sample fluids 12 remaining in the fluid separation vessel 22 therewith following collection of the aqueous phase fluid fraction 19 are removed from the fluid separation vessel 22 via a first purging fluid exit port 102 and its associated purging fluid exit line 78 as the second purging fluid 32' is introduced into the fluid separation vessel 22 through the second purging fluid entry port 98'. The second purging fluid exit port 102' is operatively positioned for recycling the second purging fluid 32' back to the second purging fluid source 30' via the second purging fluid exit line 78'.

Figure 8:
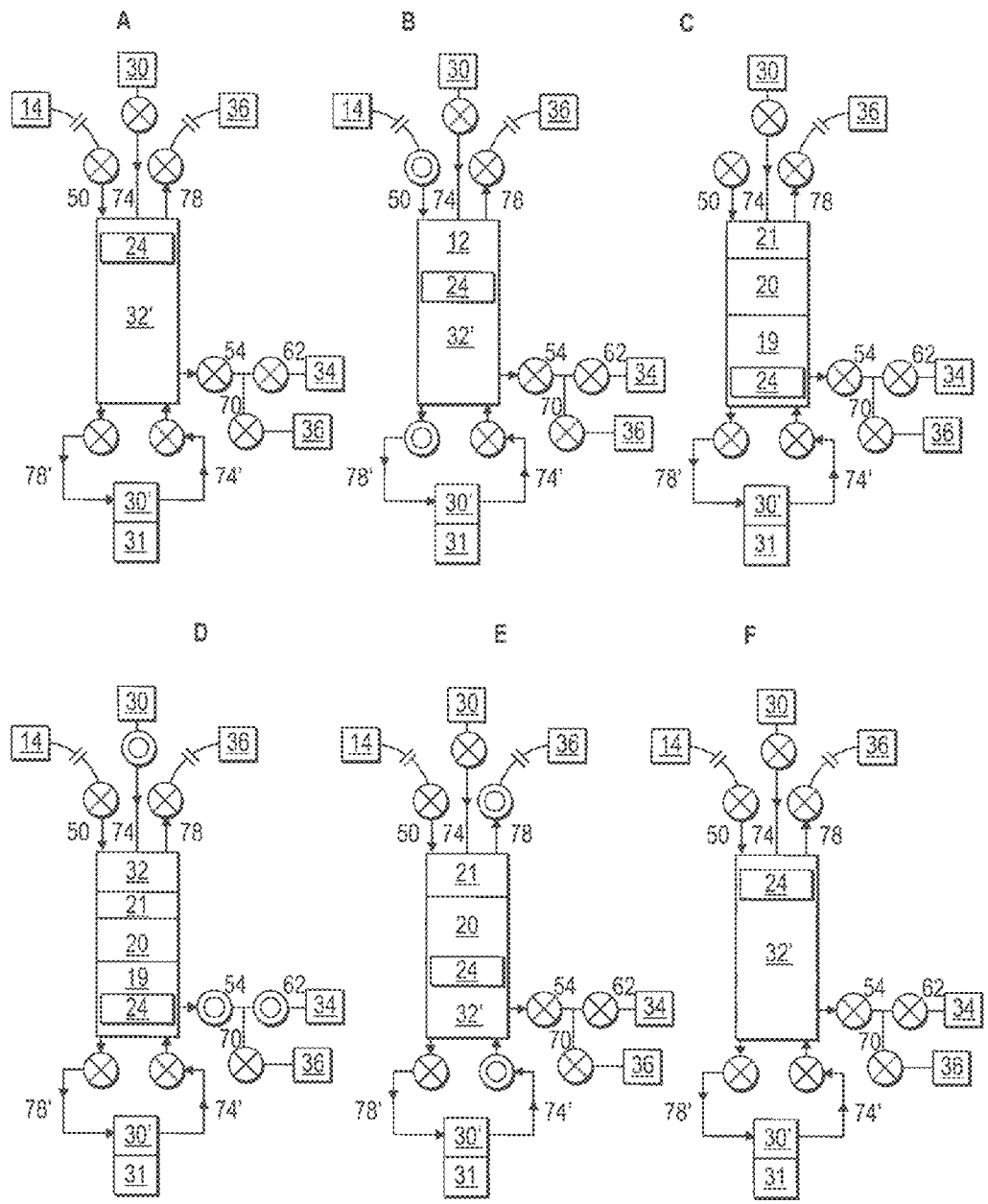
FIG. 8 depicts the sequence of steps associated with collection of an aqueous phase fluid fraction from the system depicted in FIG. 7.

To initiate an aqueous sample collection sequence using the system 10 depicted in FIG. 7, the plunger 24 is initially positioned near the top of the fluid separation vessel 22, above a filled column of the second purging fluid 32', in this case, containing liquid (As Shown in Step A of FIG. 8). At the start of a collection sequence, the controller 42 has closed the solenoid valves 82 in each of the first and second purging fluid intake lines 74, 74', each of the first and second purging fluid exit lines 78, 78', the sample fluid intake line 50, the sample fluid exit line 54, the collection vessel intake lines 62, and the first sample fluid disposal line 70 so as to prevent flow of fluids there through.

Then, as shown in Step B of FIG. 8, at a predetermined time, the controller 42 selectively opens the solenoid valves 82 in the sample fluid intake line 50 and the second purging fluid exit line 78' so that the sample fluids 12 from the sample fluid source 14 can flow through the sample fluid entry port 90 and into the fluid separation vessel 22, driving the second purging fluid 32' on the opposite side of the plunger 24 to flow out of the fluid separation vessel 22, through the second purging fluid exit port 102', through the second purging fluid exit line 78' and back to the second purging fluid source 30', thereby recycling the second purging fluid 32'. Where the second purging fluid 32' is a gas, the second purging fluid 32' is not recycled back to the second purging fluid source 30'; instead, the second purging fluid exit line 78' includes a vent 80 for expelling the gas.

Once the fluid separation vessel 22 is filled with the sample fluids 12 and the plunger 24 is displaced to the bottom of the fluid separation vessel 22, the solenoid valves 82 in all of the fluid lines directly connected to the fluid separation vessel 22, e.g., 50, 54, 70, 74, 74', 78, 78' are closed for a period of time sufficient for phase separation of the sample fluids 12 into aqueous phase 19, organic phase 20 and/or gas phase 21 fluid fractions as shown in Step C of FIG. 8.

Then, as shown in Step D of FIG. 8, the solenoid valve 82 in each of the first purging fluid intake line 74, the sample fluid exit line 54, and a predetermined collection vessel intake line 62 is opened so that as the first purging fluid 32 enters the fluid separation vessel 22 via the first purging fluid intake line 74, at least a portion of the aqueous phase fluid fraction 19 is removed from the fluid separation vessel 22 via the sample fluid exit line 54 into a collection vessel 34.

As shown in Step E of FIG. 8, upon collection of the aqueous phase fluid fraction 19, the solenoid valve 82 in each of the first purging fluid intake line 74, the sample fluid exit line 54, and the previously opened collection vessel intake line 62 is closed, and the solenoid valve 82 in each of the second purging fluid intake line 74' and the first purging fluid exit line 78 is opened so that the sample fluids remaining in the fluid separation vessel 22 above the plunger 24 are diverted to the disposal vessel 36 via the first purging fluid exit line 78 and the second sample fluid disposal line 70'. Once the second purging fluid 32' purges out all of the remaining fluids above the plunger 24 and displaces the plunger 24 to the top of the fluid separation vessel 22, all of the solenoid valves 82 are closed until the next collection sequence is initiated.

In FIG. 5, the first purging fluid entry port 110 is the same intake port connectively linking the sample fluid entry line 50 to the fluid separation vessel 22. In another embodiment, the top of the fluid separation vessel 22 may have a separate ports for the sample fluid entry line 50 and the first purging fluid intake line 74. Although the embodiment in FIG. 7 utilizes separate ports for the sample fluid entry line 50 and the first purging fluid intake line 74, other embodiments may utilize a common entry port 110 shared by the sample fluid intake line 50 and the first purging fluid intake line 74.

Similarly, other embodiments can be envisioned where multiple intake lines similarly share common entry ports as long as each intake line has its own solenoid valve upstream of the common entry port. Further, although the embodiments in FIGS. 5 and 7 introduce gas fluid 32 in the top of the fluid separation vessel 22 and liquid fluid 32' in the bottom of the fluid separation vessel, other embodiments may have gas fluids introduced in both the top and bottom portions of the fluid separation vessel instead.

In a further aspect, the present invention provides compositions and methods for collecting a gas phase fluid fraction 21 from a sample fluid source, such as a gas well.

Figure 9:
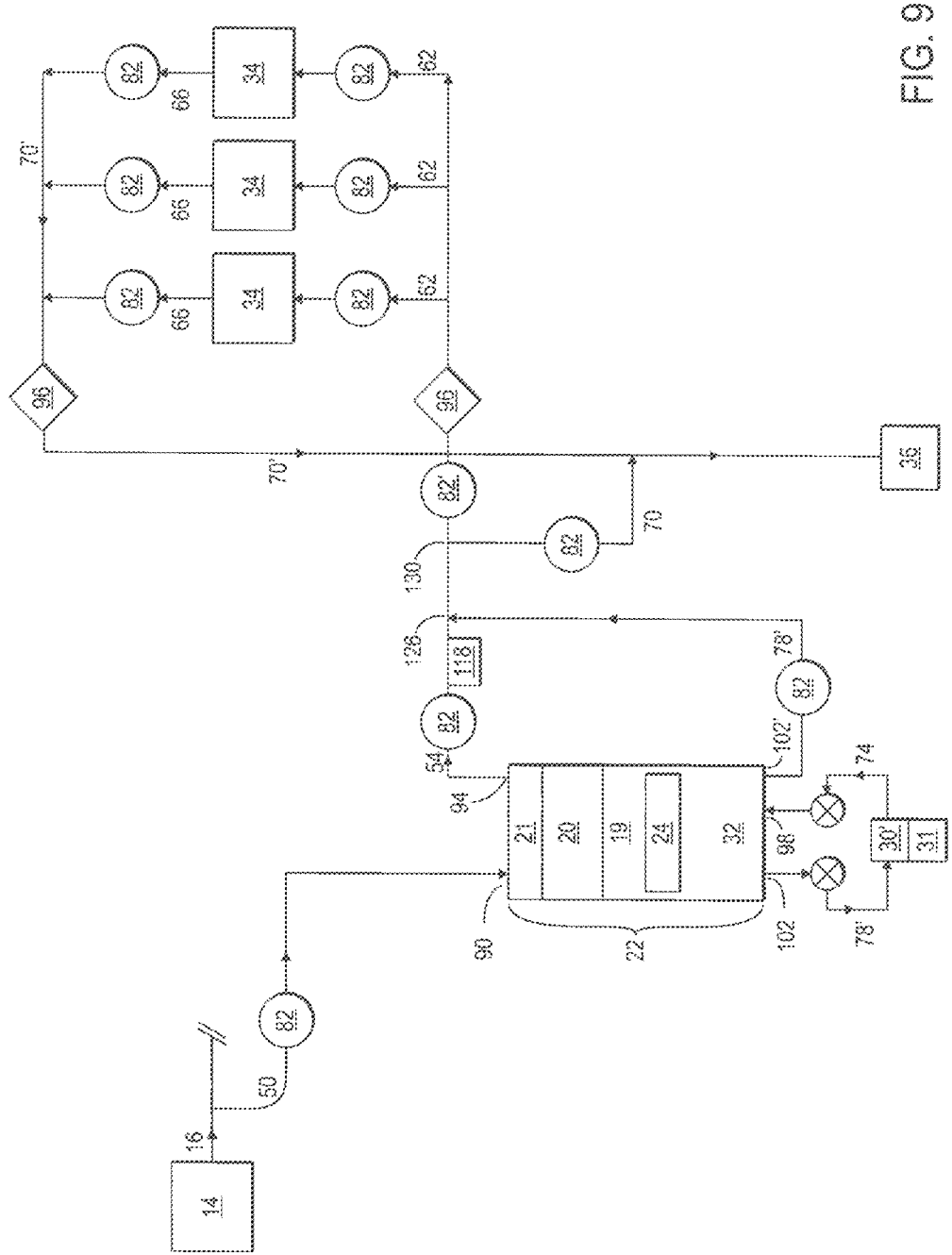
FIG. 9 is a schematic diagram of an automated gas phase fluid fraction collection system according to one embodiment.

In an exemplary embodiment depicted in FIG. 9, the sample fluid intake line 50 connectively links the pressurized line 16 to a sample fluid entry port 90 disposed in the top of the fluid separation vessel 22. The purging fluid intake line 74 connectively links the purging fluid source 30 to a purging fluid entry port 98 disposed in the bottom of the fluid separation vessel 22. A sample fluid exit line 54 connectively links a sample fluid exit port 94 disposed in the top of the fluid separation vessel 22 to the collection vessel 34 and/or a collection vessel intake line 62 (where a plurality of collection vessels 34 is employed). A first sample fluid disposal line or bypass line 70 connectively links the sample fluid exit line 54 to a second sample fluid disposal line 70' connectively linking a collection vessel 34 or plurality of collection vessel exit lines 66 to the disposal vessel 36. As shown in FIG. 9, the first sample fluid disposal line 70 extends from a second branchpoint 130 in the sample fluid exit line 54 and is used for removing the aqueous 19 and organic 20 phase fluid fractions as the purging fluid 32 from the purging fluid source 30 is introduced through the bottom of the fluid separation vessel 22.

A purging fluid exit line 78 connectively links a purging fluid exit port 102 disposed in the bottom of the fluid separation vessel 22 to the purging fluid source 30. A solenoid valve 82 is operatively linked to each of the sample fluid intake line 50, the sample fluid intake line 50, the sample fluid exit line 54, the purging fluid intake line 74, the purging fluid exit line 78, and each of the collection vessel intake lines 62. Where the system 10 includes a plurality of collections vessels 34 and collection vessel intake lines 62, a second solenoid valve 82' is operatively linked to the sample fluid exit line 54 between the distal branchpoint 130 and the disconnect 96 upstream of the most proximal collection vessel intake line 62 as shown in FIG. 9.

A liquid catch can 118 for dehydrating gas phase fluids flowing therethrough may be operatively linked to the sample fluid exit line 54 between the proximal solenoid valve 82 and the proximal branchpoint 126 in the sample fluid exit line 54 and the collection vessel 34 or collection vessel intake line 62.

In one embodiment, the purging fluid source 30 contains a purging fluid 32 comprising liquid and the purging fluid exit line 78 connectively links a purging fluid exit port 102 disposed in the bottom of the fluid separation vessel 22 to the purging fluid source 30 so that the purging fluid 32 can be recycled back to the purging fluid source 30 as the sample fluids 12 are received into the fluid separation vessel 22 from the sample fluid source 14 through the sample fluid entry port 90.

In another embodiment, the purging fluid source 30 contains compressed gas and the purging fluid exit line 78 extends from the purging fluid exit port 102, whereby the purging fluid exit line contains a vent 80 positioned so that the gas can be released into the atmosphere as the sample fluids 12 are received into the fluid separation vessel 22 from the sample fluid source 14 through the sample fluid entry port 90.

To initiate a gas phase sample collection sequence using the system 10 depicted in FIG. 9, the plunger 24 is initially positioned near the top of the fluid separation vessel 22, above a filled column of the purging fluid 32, such as a liquid. At the start of a collection sequence, the controller 42 has closed the solenoid valves 82 in each of the sample fluid intake line 50, sample fluid exit line 54, purging fluid intake line 74, and purging fluid exit line 78 so as to prevent flow of fluids therethrough. Where the system 10 includes a plurality of collections vessels 34 and collection vessel intake lines 62, solenoid valves 82 in each of the collection vessel intake lines 62 are closed, as well as the distal solenoid valve 82' in the sample fluid exit line 54.

Then, at a predetermined time, the controller 42 selectively opens the solenoid valves 82 in the sample fluid intake line 50 and the purging fluid exit line 78 so that the sample fluids 12 from the sample fluid source 14 can flow through the sample fluid entry port 90 and into the fluid separation vessel 22, driving the purging fluid 32 on the opposite side of the plunger 24 to flow out of the fluid separation vessel 22, through the purging fluid exit port 102, through the purging fluid exit line 78 and back to the purging fluid source 30, recycling the purging fluid 32 therein. Where the purging fluid 32 is a gas, the purging fluid 32 is not recycled; instead, the purging fluid exit line 78 is configured to include a vent 80 for expelling the gas.

Once the fluid separation vessel 22 is filled with the sample fluids 12 and the plunger 24 is displaced to the bottom of the fluid separation vessel 22, the solenoid valves 82 in all of the fluid lines directly connected to the fluid separation vessel 22, e.g., 50, 54, 74, and 78 are closed for a period of time sufficient for phase separation of the sample fluids 12 into aqueous phase 19, organic phase 20 and/or gas phase 21 fluid fractions.

Alternatively, the fluid separation vessel 22 may be filled while the sample fluid exit line 54 is flushed or cleaned with the purging fluid 32 by closing the proximal solenoid valve 82 in the sample fluid exit line 54, the purging fluid intake line 74, and the purging fluid exit line 78 so as to prevent flow of fluids therethrough; and opening the sample fluid intake line 50 and a second purging fluid exit line 78' connectively linking the bottom of the fluid separation vessel 22 via a second purging fluid exit port 102' to the sample fluid exit line 54, where the second purging fluid exit line 78' further includes a solenoid valve 82 regulating flow of fluids therethrough. In this case, as the sample fluids 12 from the sample fluid source flow 14 through the sample fluid entry port 90 into the fluid separation vessel 22, purging fluid 32 on the other side of the plunger 24 is driven out of fluid separation vessel 22, through the sample fluid exit line 54, the first sample fluid disposal line 70 and into the disposal vessel 36.

Where the system 10 is configured for collecting a plurality of sample fluid fractions as depicted in FIG. 9, the distal solenoid valve 82' in the sample fluid exit line 54 is also closed. Following the phase separation of sample fluids 12, solenoid valves 82, 82' in each of the purging fluid intake line 74, both solenoid valves 82, 82' in the sample fluid exit line 54, and a predetermined collection vessel intake line 62 are opened so that as the purging fluid 32 enters the fluid separation vessel 22 via the purging fluid intake line 74, at least a portion of the gas phase fluid fraction 21 is removed from the fluid separation vessel 22 via the sample fluid exit line 54 into a collection vessel 34.

Upon collection of the gas phase fluid fraction 21, the solenoid valve 82 in the first sample fluid disposal line 70 is opened, the solenoid valve 82 in the previously opened collection vessel intake line 62 is closed, and the distal solenoid valve 82' in the sample fluid exit line 54 is closed so that the sample fluids remaining in the fluid separation vessel 22 above the plunger 24 are diverted to the disposal vessel 36 as depicted in FIG. 9. Once the purging fluid 32 drives out all of the remaining fluids above the plunger 24 and displaces the plunger 24 to the top of the fluid separation vessel 22, all of the solenoid valves 82 are closed until the next collection sequence is initiated.

In a further aspect, the present invention provides compositions and methods for collecting an organic phase fluid fraction 20 from a sample fluid source 14.

Figure 10:
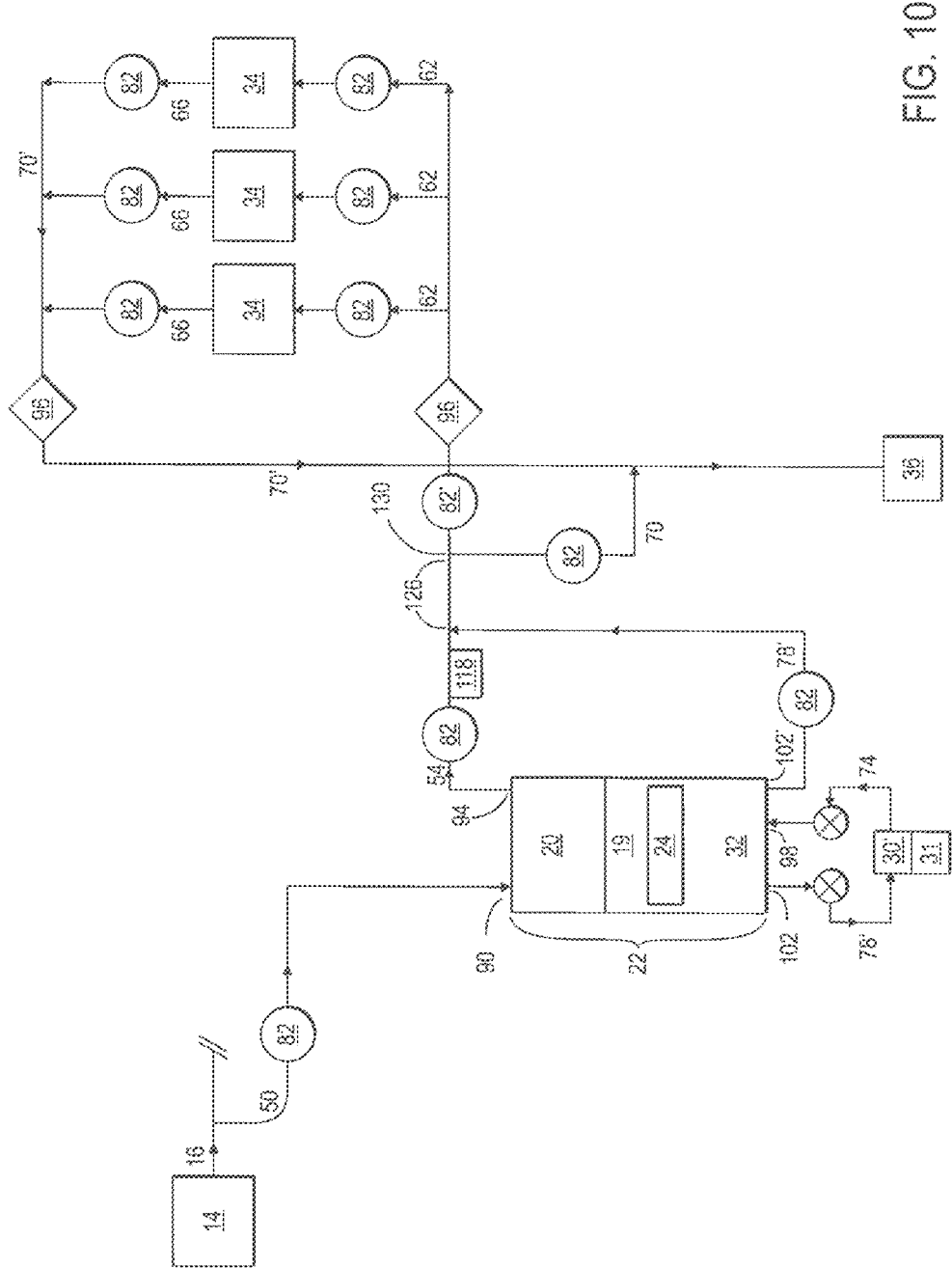
FIG. 10 is a schematic diagram of an automated organic phase fluid fraction collection system according to one embodiment.

In an exemplary embodiment depicted in FIG. 10, the sample fluid intake line 50 connectively links the pressurized line 16 to a sample fluid entry port 90 disposed in the top of the fluid separation vessel 22. The purging fluid intake line 74 connectively links the purging fluid source 30 to a purging fluid entry port 98 disposed in the bottom of the fluid separation vessel 22. The purging fluid exit line 78 connectively links a purging fluid exit port 102 disposed in the bottom of the fluid separation vessel 22 to the purging fluid source 30. A sample fluid exit line 54 connectively links a sample fluid exit port 94 disposed in the top of the fluid separation vessel 22 to the collection vessel 34 or a collection vessel intake lines 62 connectively linked to a corresponding collection vessel 34. A first sample fluid disposal line or bypass line 70 connectively links the sample fluid exit line 54 to a second sample fluid disposal line connectively linking a collection vessel 34 or plurality of collection vessel exit lines 66 to the disposal vessel 36. As shown in FIG. 10, the first sample fluid disposal line 70 extends from a second branchpoint 130 in the sample fluid exit line 54 and is used for removing the gas phase fluid fraction 21 and the aqueous phase fluid fraction 19 as the purging fluid 32 from the purging fluid source 30 is introduced through the bottom of the fluid separation vessel 22.

FIG. 10 depicts a system 10 containing a plurality of collections vessels 34, collection vessel intake lines 62 and collection vessel exit lines 66. Each of the sample fluid intake line 50, the purging fluid intake line 74, the first purging fluid exit line 78, the second purging fluid exit line 78', the sample fluid exit line 54, the first sample fluid disposal line 70, the second sample fluid disposal line 70,' the collection vessel intake lines 62, and the collection vessel exit lines 66 include a solenoid valve 82 controlling flow of fluids therethrough.

In certain embodiments, a pressure relief valve may substitute for the solenoid valve 82 in each of the collection vessel exit lines 66. The system may further include a pressure relief valve in the second sample fluid disposal line 70', downstream of the most distal collection vessel exit line 66.

The sample fluid exit line 54 may further include a capillary viscometer 122 between the proximal solenoid valve 82 and the first branchpoint 126. The capillary viscometer 122 is configured to measure the pressure differential of sample fluids 12 flowing though the sample fluid exit line 54 so that gases in the gas phase fluid fraction 21 can be diverted to the disposal vessel 36 via the first sample fluid disposal line or bypass line 70 prior to collection of the organic phase fluid fraction 20.

To initiate an organic phase sample collection sequence using the system 10 depicted in FIG. 10, the plunger 24 is initially positioned near the top of the fluid separation vessel 22, above a filled column of the purging fluid 32, in this case, containing liquid. At the start of a collection sequence, the controller 42 has closed the solenoid valves 82 in the sample fluid intake line 50, the sample fluid exit line 54, the purging fluid intake line 74, and the purging fluid exit lines 78 so as to prevent flow of fluids therethrough. Where the system 10 includes a plurality of collections vessels 34 and collection vessel intake lines 62, solenoid valves 82 in each of the collection vessel intake lines 62, sample collection vessel exit lines 66, and/or the second solenoid valve 82' in the sample fluid exit line 54 may be closed as well.

Then, at a predetermined time, the controller 42 selectively opens the solenoid valves 82 in the sample fluid intake line 50 and the purging fluid exit line 78 so that the sample fluids 12 from the sample fluid source 14 can flow through the sample fluid entry port 90 and into the fluid separation vessel 22, driving the purging fluid 32 on the opposite side of the plunger 24 to flow out of the fluid separation vessel 22, through the purging fluid exit port 102, through the purging fluid exit line 78 and back to the purging fluid source 30, recycling the purging fluid 32 therein.

Alternatively, the fluid separation vessel 22 may be filled while the sample fluid exit line 54 is flushed or cleaned with the purging fluid 32 by closing the proximal solenoid valve 82 in the sample fluid exit line 54, the purging fluid intake line 74, and the first purging fluid exit line 78 so as to prevent flow of fluids therethrough; and opening the sample fluid intake line 50 and a second purging fluid exit line 78' connectively linking the bottom of the fluid separation vessel 22 via a second purging fluid exit port 102' to the sample fluid exit line 54. In this case, the second purging fluid exit line 78' also includes a solenoid valve 82 regulating flow of fluids therethrough. As sample fluids 12 from the sample fluid source 14 flow through the sample fluid entry port 90 into the fluid separation vessel 22, purging fluid 32 on the other side of the plunger 24 is driven out of fluid separation vessel 22, through the sample fluid exit line 54, the first sample fluid disposal line 70 and into the disposal vessel 36.

Once the fluid separation vessel 22 is filled with the sample fluids 12 and the plunger 24 is displaced to the bottom of the fluid separation vessel 22, the solenoid valves 82 in at least all of the fluid lines directly connected to the fluid separation vessel 22, e.g., 50, 54, 74, and 78 are closed for a period of time sufficient for phase separation of the sample fluids 12 into aqueous phase 19, organic phase 20 and/or gas phase 21 fluid fractions. Where the system 10 is configured for collecting a plurality of organic phase 20 fluid fractions as depicted in FIG. 10, the second solenoid valve 82' in the sample fluid exit line 54 is also closed.

Following phase separation of the sample fluids 12, solenoid valves 82 (where included) in each of the purging fluid intake line 74, the proximal portion of the sample fluid exit line 54, and the first sample fluid disposal line 70 are opened so that as the purging fluid 32 enters the fluid separation vessel 22 via the purging fluid intake line 74, the gas phase fluid fraction 21 flows out of the fluid separation vessel 22, through the proximal portion of the sample fluid exit line 54, through the first sample fluid disposal line 70 and into the disposal vessel 36.

After the gas phase fluids 21 have been removed or the capillary viscometer 122 has detected a change in the pressure of fluids passing through the sample fluid exit line 54 indicative of the presence of organic phase fluids passing through the viscometer, the solenoid valve 82 in the first sample fluid disposal line 70 is closed, the distal solenoid valve 82' in the sample fluid exit line 54 is opened, and a selected collection vessel intake line 62 is opened so that at least a portion of the organic phase fluid fraction 20 flowing though the sample fluid exit line 54 may be collected in a sample fluid collection vessel 34 operatively linked to the selected collection vessel intake line 62.

Where the organic sample collection system 10 includes a single collection vessel 34, the distal solenoid valve 82' in the sample fluid exit line 54 is initially closed and the gas phase fluid fraction 21 is diverted to the sample fluid disposal vessel 34 via the first sample fluid disposal line 70 feeding into the second sample fluid exit line 70' or suitable disposal vessel 36. Then, the first sample fluid disposal line 70 is closed and the distal solenoid valve 82' in the sample fluid exit line 54 is opened so that at least a portion of the organic phase fluid fraction 20 may flow though the sample fluid exit line 54 and into the sample fluid collection vessel 34.

Upon collection of the organic phase fluid fraction 20, the distal solenoid valve 82' in the in the sample fluid exit line 54 is closed and the solenoid valve 82 in the first sample fluid disposal line 70 is opened so that the sample fluids remaining in the fluid separation vessel 22 above the plunger 24 are diverted to the disposal vessel 36 via the first sample fluid disposal line 70.

In a further aspect, a method for assembling an automated fluid sampling system 10 includes the steps of operatively linking:

(a) a pressurized line 16 to a plunger 24 equipped fluid separation vessel 22 by a sample fluid intake line 50, the pressurized line 16 being operatively linked to a sample fluid source 14 comprising sample fluids 12;

(b) the plunger 24 equipped fluid separation vessel 22 to a sample fluid exit line 54, a purging fluid intake line 74, and a purging fluid exit line 78;

(c) the sample fluid exit line 54 to a first sample fluid disposal line 70, and a plurality of collection vessel intake lines 62;

(d) a second sample fluid disposal line 70' to a disposal vessel 36;

(e) the first sample fluid disposal line 70 to a disposal vessel 36 or the second sample fluid disposal line 70';

(f) each of the collection vessel intake lines 62 to a collection vessel 34;

(g) each of the collection vessels 34 to one of a plurality of collection vessel exit lines 66;

(h) each of the plurality of collection vessel exit lines 66 to the second sample fluid disposal line 70';

(i) a solenoid valve to each of the sample fluid intake line 50, the sample fluid exit line 54, the first sample fluid disposal line 70, the purging fluid intake line 74, the purging fluid exit line 78, and each of the pluralities of collection vessel intake lines 62 and collection vessel exit lines 66, each solenoid valve being configured to selectively control fluid flow therethrough; and (j) a controller 42 to the solenoid valves 82 so that each of the solenoid valves 82 is capable of being selectively opened or closed in a predetermined manner.

The automated sampling system 10 is particularly useful for automated tracer samplings from production wells and/or injection wells in oil well and/or gas well fields. The automated system 10 may be located on a ground surface onshore, above the reservoir or it may be located on an offshore surface such as above a deep water drilling site. In this embodiment, the automated system 10 may be a skid system packaged into a single unit.

Figure 11:
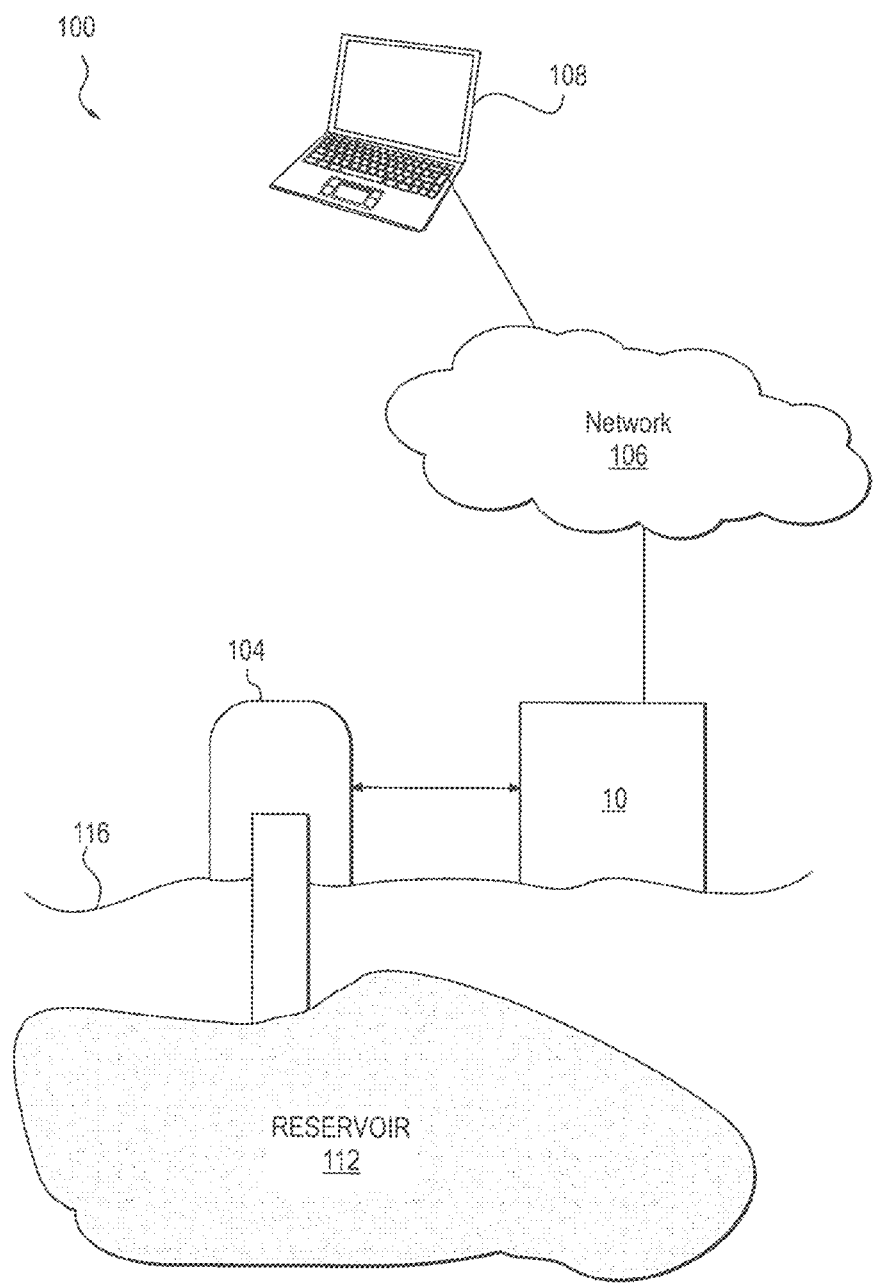
FIG. 11 is a schematic block diagram of an automated tracer sampling and measurement system.
Figure 12:
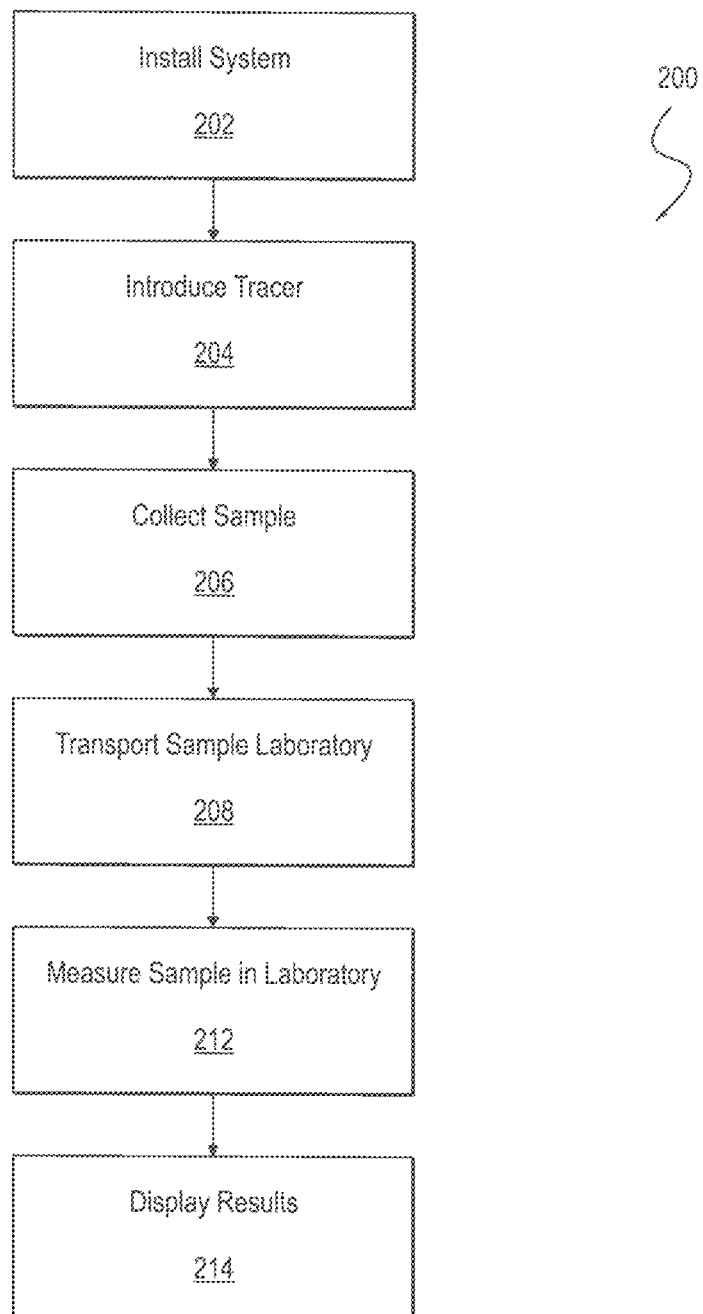
FIG. 12 is a flow chart of a non-integrated method for performing tracer measurement.

FIG. 11 is a schematic block diagram illustrative of a system 100 using an automated tracer sampling and measurement system 10. In this example embodiment, the system 100 includes an automated tracer sampling and measurement system (hereinafter automated system) 10 located near a sample fluid source 14, such as a production well or injection well. In this embodiment, the sample fluid source 14 and automated system 10 are located on a ground surface 116 onshore, above a reservoir 112. In other embodiments, the sample fluid source 14 and automated system 10 are located on an offshore surface such as above a deep water drilling site.

In this embodiment, the automated system 10 is a skid system packaged into a single unit. One or more computing devices 108 may be used to automate various processes in the automated system 10. The computing devices 108 may communicate in wireless communication with the automated system 10. In some embodiments, the automated system 10 may be powered by a local power source such as a variety of solar panels connected thereto. In other embodiments, electrical components of the automated system 10 are powered using one or more batteries, generators, or other types of power supplies.

In this embodiment, the sample fluid source 14 provides a structural interface for extracting fluids from the reservoir 112. Example fluids that flow in a reservoir are oil, water, gas, or a combination thereof. The automated system 10 is located near and connected to a wellhead at the sample source 104. In some embodiments, the automated system 10 is connected to the sample fluid source 14 using a series of pipes appropriate for extracting fluid samples from the sample fluid source 14. In other embodiments, other connection interfaces are used.

In this embodiment, the computing devices 108 can be used to automate the one or more processes of the present disclosure. The computing devices 108 can also be used to display measurement results and/or a status of the automated system 10. Additionally, a single computing device 108 can be linked to one or more automated systems 10. The computing devices 108 can be any one of a variety of computing devices including, but not limited to a desktop computing device, a mobile computing device (such as a laptop, smartphone, tablet computer, and the like), or it can be another type of computing device.

Similarly, the automated system 10 provides data to, and receives data from, one or more computing devices 108 over the data communication network 106. The data communication network 106 can be any variety of communication networks including, but not limited to a wide area network such as the Internet, a local area network, or any other Internet based network.

With regard to the controller 42, various computing systems can be used to manage the flow of fluids in connection with sample collection and processing. For example, embodiments of the disclosure may be practiced in various types of electrical circuits comprising discrete electronic elements, packaged or integrated electronic chips containing logic gates, a circuit utilizing a microprocessor, or on a single chip containing electronic elements or microprocessors. Embodiments of the disclosure may also be practiced using other technologies capable of performing logical operations such as, for example, AND, OR, and NOT, including but not limited to mechanical, optical, fluidic, and quantum technologies. In addition, aspects of the methods described herein can be practiced within a general purpose computer or in any other circuits or systems.

Embodiments of the present disclosure can be implemented as a computer process (method), a computing system, or as an article of manufacture, such as a computer program product or computer readable media. The computer program product may be a computer storage media readable by a computer system and encoding a computer program of instructions for executing a computer process. Accordingly, embodiments of the present disclosure may be embodied in hardware and/or in software (including firmware, resident software, micro-code, etc.). In other words, embodiments of the present disclosure may take the form of a computer program product on a computer-usable or computer-readable storage medium having computer-usable or computer-readable program code embodied in the medium for use by or in connection with a sample collection sequence.

The present disclosure provides an integrated approach to sampling, processing, and measuring tracers in a reservoir or aquifer which automates one or more steps in the process. The systems and methods, according to the present disclosure, solve at least some of the aforementioned problems of sample contamination, operator burden, cost, and delay associated with the current system frequently caused by manual tasks. In some embodiments of the present disclosure, an automated solution is installed as an integrated inline system at or near a wellhead or production manifold. The integrated inline system can be incorporated into existing onshore or offshore wellhead configurations. This embodiment also works reliably and durably in harsh oilfield environments. Because of task automation, the cost of the system is equal to or less than the cost of the current practice of tracer sampling. The terms "automatic" and "automated" denote functions and processes that can be conducted using tools and mechanisms, directed by a computing device, that do not physically require human effort to accomplish. For example, in existing systems, a field operator extracts samples from a wellhead. The automated approach discussed herein allows the system 10 to automatically collect and process samples at pre-established intervals, thereby eliminating the need for the field operator to manually extract and process the sample from the wellhead. In addition, one or more steps or processes can be automated, allowing for simpler (and less time-intensive) tracer measurement.

Tracers that may be introduced into the reservoir or aquifer in use with the above described systems include, but are not limited to fluorinated benzoic acids (FBAs), fluorescein dyes, a FBA/fluorescein synthesis, fluorescing nanocrystals, radioactive tracers, fluorescing nanoparticles, and a LUX Assure Tracer™. FBAs demonstrate low detection points whereas radioactive tracers can be measured without the need to separate phases in a sample. Magnetic nanoparticle tracers have detection thresholds as low as 1 part per billion (ppb) and can be used to distinguish other produced solids. In some embodiments, the type of tracer injected in the reservoir has a low rate of absorption upon the formation rock. Methods for sample analysis, processing and tracer testing are described in U.S. Patent Application Publication No. 2014/0260694 to Szendak, the disclosures of which are incorporated by reference herein.

FIG. 11 is a flow chart illustrating a non-integrated method 200 of performing tracer measurement. The method 200 includes installation of a system (step 202), introduction of a tracer (step 204), collection of at least one sample (step 206), transportation of the sample(s) to an externally located laboratory (step 208), filtration of the sample(s) in the laboratory (step 210), measurement of the sample(s) for tracers (step 212) in the laboratory, and display of results (step 214).

In this embodiment, the install system (step 202) involves an initial installation of the system 10 at a wellhead or production manifold. Following the system 10 install (step 202) and introduction of a tracer (step 204) into the reservoir, an operator collects one or more one aqueous phase 19, organic phase 20 or gas phase 21 fluid samples from the system 10. Following collection of at least one sample (step 206), the operator transports the sample(s) to a laboratory (step 208) located away from the system 10 location. The laboratory technician then measures one of the separated phases in the laboratory (step 212) for tracer concentration using a tracer measurement device.

In some embodiments, the tracer measurement device used in the laboratory is a high performance liquid chromatography device. In other embodiments, a laboratory operator measures the concentration of the tracer in the sample using a spectroscope measurement device or other appropriate device capable of detecting fluorescence tracers. The measurement device then displays the results of the concentration of tracers found in the sample.

Figure 13:
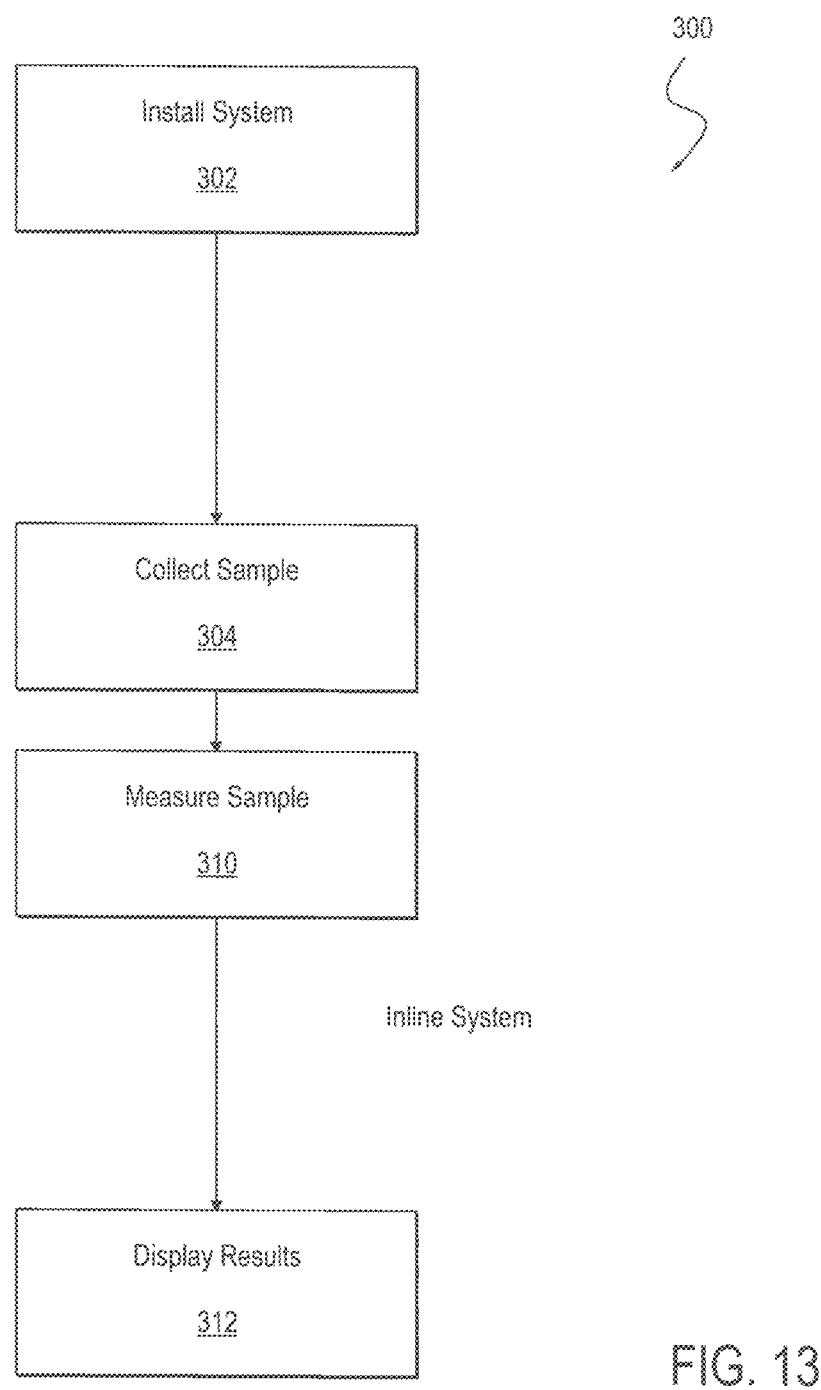
FIG. 13 is a flow chart of a method used by an automated tracer sampling and measurement system.

FIG. 13 is a flow chart of a method used by the automated sampling system 10. This exemplary embodiment describes a method 300, used by a computing device, for performing tracer measurements in an automated and integrated embodiment. The method 300 includes installing the system (step 302), collecting at least one sample (step 304), measuring the sample (step 310), and displaying results (step 312).

In this embodiment, system install (step 302) involves the initial installation of the automated system 10 at or near the wellhead or production manifold. The automated system 10 may be in the form of a skid system that is packaged as a single unit and capable of being easily installed into the current wellhead design. In some embodiments, the automated system 10 can be uninstalled, relocated, and re-installed, using a flatbed truck or other means of transport, into other wellhead or production manifold structures. Once the system is physically in place, installing the system (step 302) further involves extracting a sample of fluid to ensure that the automated system 10 captures a sample containing more than 10% water so that the measurement device can accurately detect the presence and concentration of a tracer. Installing the system (step 302) may further involve installing a transport system for transferring collected samples to a measurement device using a conveyor as described above, or other device.

The measurement device measures the sample(s) (step 310) for tracers. In this embodiment, the measurement device used is a fluorometer or a fiber optic fluoro-spectroscope. In other embodiments, other types of measurement devices are used. In some embodiments, the measurement device is connected to a data communication network.

Types of measurement devices that can be used include, but are not limited to laboratory spectroscopes, fiber optic fluoro-spectroscopes, Hall Effect sensors, fluorometers, Geiger counters, gas chromatography measurement devices, and post column reaction spectroscopes. In some embodiments, the tracer measurement device can detect fluorescent type tracers below 50 ppb. The type of measurement device used by the systems 10 depends on the type of tracer injected into the reservoir or aquifer.

Alternative embodiments may use a magnetic nanoparticle tracer in combination with a Hall Effect sensor measurement device. Another alternative embodiment uses a radioactive tracer in combination with a Geiger counter measurement device. Additionally, some measurement methods will require a clean, aqueous phase sample with no formation solids or oil-water emulsions. Other embodiments require control of salinity or pH levels.

In some embodiments, once measuring at least one sample (step 310) is completed, the measurement device automatically sends tracer concentration results, over the data communication network, to a computing device that displays the results (step 312). In some embodiments, the results are stored on a database computing device. In some embodiments, the measured sample may be pumped back to the wellhead.

The method used by the automated system 10 can be fully automated or partially automated. In some embodiments, steps 304-312 are all automated, thereby requiring little to no human intervention. In other embodiments, the automated system 10 is partially automated, thereby allowing some human interaction. In some example embodiments, measuring the sample (step 310) is not automated and performed by an operator.

Figure 14:
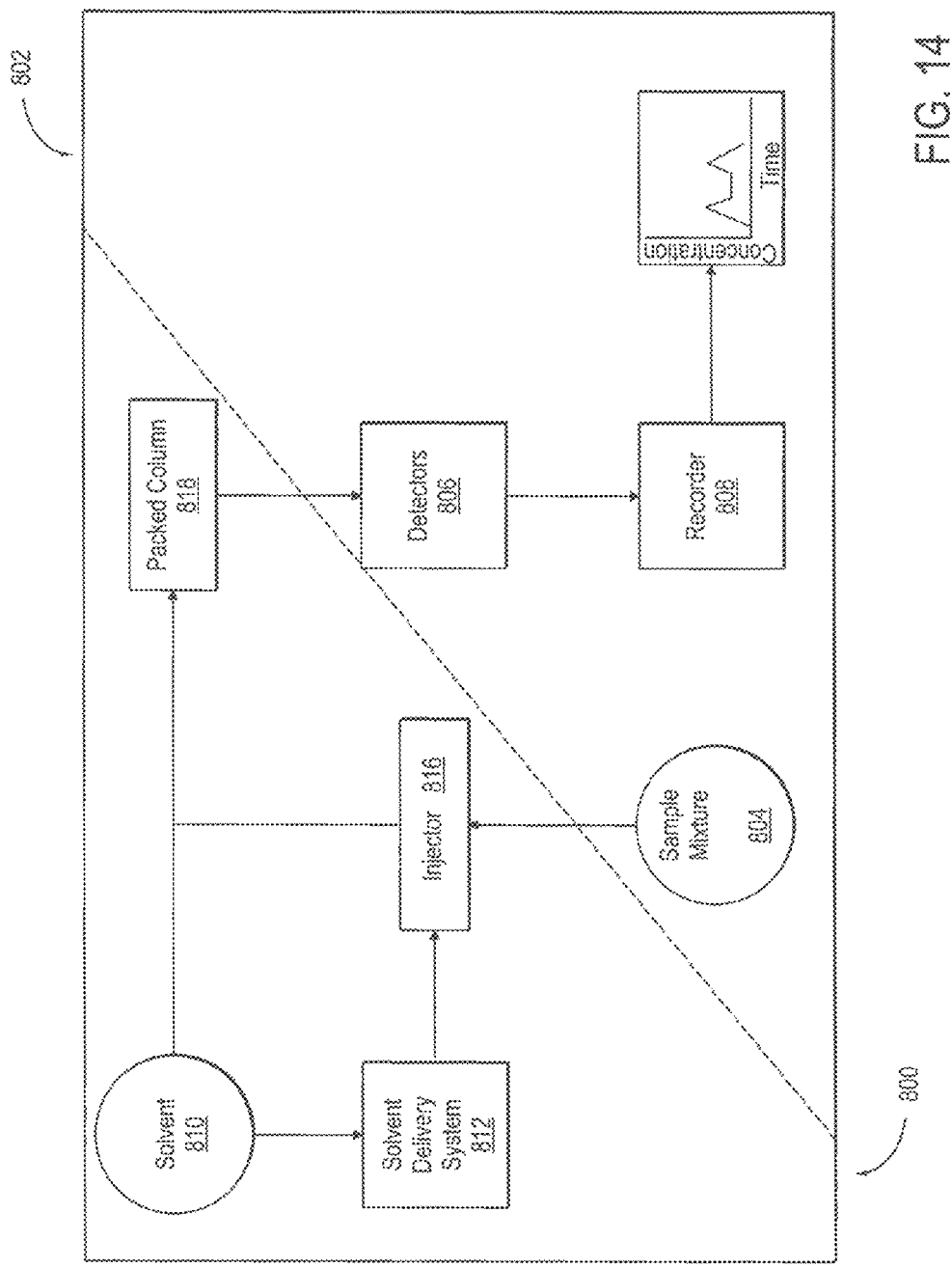
FIG. 14 is a flow chart of a tracer measurement device used by an automated tracer sampling and measurement system.

FIG. 14 is a flow chart of two alternative tracer measurement devices 800 used by the automated system 10. FIG. 14 is divided into two main types of tracer measurement devices: a high performance liquid chromatography (HPLC) measurement device 800 and a fluorescence spectroscope 802 used by an embodiment. In this embodiment, the fluorescence spectroscope 802, which is represented by the components below the dashed line, accepts a sample mixture 804 and processes the sample 804 using a series of detection components 806. The detection components 806 are responsible for detecting and measuring the fluorescein tracer concentration in the sample 804. The results are recorded using a recording device 808 as a function of concentration over time. In addition to the fluorescence spectroscope 802, an HPLC measurement device 800 (including features depicted above the dashed line) uses a liquid 810, a liquid delivery system 812, packed columns 818, and an injector 816.

Referring generally to FIGS. 1-14, the various embodiments discussed herein are particularly adapted or adaptable to aqueous phase, organic phase and gas phase measurement of tracers. The various embodiments described above are provided by way of illustration only and should not be construed to limit the claims attached hereto. Those skilled in the art will readily recognize various modifications and changes that may be made without following the example embodiments and applications illustrated and described herein, and without departing from the true spirit and scope of the following claims.

The invention claimed is:

1. An automated fluid sampling system comprising:
   a pressurized line connectively linked to a sample fluid source comprising sample fluids, where the sample fluid source is a production well or injection well;
   a fluid separation vessel receiving the sample fluids from the pressurized line, the fluid separation vessel configured for gravity-mediated phase separation of the sample fluids into at least two of: (a) an aqueous phase fluid fraction, (b) an organic phase fluid fraction, and (c) a gas phase fluid fraction, the fluid separation vessel comprising a plunger for collecting sample fluids in the fluid separation vessel and purging fluids from the fluid separation vessel, where a plurality of inlet ports and a plurality of outlet ports are disposed in top, bottom or side portions of the fluid separation vessel for mediating flow of sample fluids therethrough;
   a purging fluid source comprising a purging fluid, the purging fluid comprising a gas or liquid, the purging fluid source being operatively linked to a pump;
   a sample fluid collection vessel for receiving sample fluids from the fluid separation vessel;
   a disposal vessel for receiving sample fluids purged from the fluid separation vessel;
   a plurality of fluid lines comprising solenoid valves controlling flow of fluids therethrough, where the plurality of fluid lines operatively link the fluid separation vessel to the pressurized line, the purging fluid source, the sample fluid collection vessel, and the disposal vessel for filling the fluid separation vessel with the sample fluids, collecting a phase separated fluid fraction into the sample fluid collection vessel, purging fluid remaining in the fluid separation vessel following collection of the phase separated fluid fraction, removing sample fluids purged from the fluid separation vessel into the disposal vessel, recycling a purging fluid into its corresponding fluid source, flushing one or more fluid lines downstream of the fluid separation vessel, or a combination thereof; and
   a controller configured to manage the flow of fluids through the fluid sampling system in a predetermined manner.

2. The system of claim 1, further comprising a filtration system between the pressurized line and the fluid separation vessel for removing solids, salts, and other formations from the sample fluids.

3. The system of claim 1, further comprising a plurality of sample fluid collection vessels, each connectively linked to a collection vessel intake line extending from the sample fluid exit line.

4. The system of claim 3, wherein the plurality of sample fluid collection vessels are housed as an array in a sample box.

5. The system of claim 3, further comprising a sample fluid intake line, a sample fluid exit line, a first sample fluid disposal line, a second sample fluid disposal line, a purging fluid intake line, and a purging fluid exit line, wherein:
   the sample fluid intake line operatively links the pressurized line to the fluid separation vessel;
   the sample fluid exit line operatively links the fluid separation vessel to a first sample fluid disposal line and each of the plurality of collection vessel intake lines;
   the first sample fluid disposal line operatively links the sample fluid exit line to the disposal vessel or the second sample fluid disposal line;
   the second sample fluid disposal line operatively links the disposal vessel to the first sample fluid disposal line and the plurality of collection vessel exit lines, where each collection vessel exit line is operatively linked to a collection vessel;
   each collection vessel intake line is operatively linked to a collection vessel, where the sample fluid exit line comprises proximal and distal solenoid valves controlling flow of fluids therethrough, including a branchpoint between the proximal and distal solenoid valves connectively linking the sample fluid exit line and the first sample fluid disposal line;
   the purging fluid intake line operatively links the purging fluid source to the fluid separation vessel;
   the purging fluid exit line operatively links the fluid separation vessel to the second sample fluid disposal line or vent to the atmosphere;
   each of the sample fluid intake line, the plurality of collection vessel intake lines, the plurality of collection vessel exit lines, the purging fluid intake line, the purging fluid exit line, and the first sample fluid disposal line comprises a solenoid valve controlling flow of fluids therethrough; and wherein the controller is configured to open or close each of the solenoid valves in each of the sample fluid intake line, the sample fluid exit line, the plurality of collection vessel intake lines, the plurality of collection vessel exit lines, the purging fluid intake line, the purging fluid exit line, and the first sample fluid disposal line in a predetermined manner.

6. The system of claim 5, wherein the fluid separation vessel comprises:
a sample fluid entry port positioned for receiving sample fluids from the pressurized line;
a sample fluid exit port positioned for removing phase separated fluid fractions from the fluid separation vessel via the sample fluid exit line;
a purging fluid entry port positioned for receiving a purging fluid from the purging fluid source via the purging fluid intake line to facilitate collection of the phase separated fluid fraction, purging of sample fluids remaining in the fluid separation vessel following collection of the phase separated fluid fraction, or both; and
a purging fluid exit port positioned for removing a purging fluid or sample fluids remaining in the fluid separation vessel following removal of the phase separated fluid fraction from the fluid separation vessel via the purging fluid exit line and collection of the phase separated fluid fraction into the collection vessel.

7. The system of claim 6, further comprising a second purging fluid source comprising a second purging fluid, the second purging fluid source being operatively linked to a second pump where the second purging fluid source comprises a liquid;
where the fluid separation vessel further comprises a second purging fluid entry port and a second purging fluid exit port through which the second purging fluid can be recycled back to second purging source via a second purging fluid exit line following collection of the phase separated fluid fraction.

8. The system of claim 6, wherein the pluralities of inlet ports, outlet ports, and fluid lines are operatively positioned for collecting an aqueous phase fluid fraction in a sample fluid collection vessel.

9. The system of claim 8, wherein:
the sample fluid entry port is disposed in a bottom portion of the fluid separation vessel;
the sample fluid exit port is disposed in a bottom portion or side portion of the fluid separation vessel; and
the purging fluid entry port and the purging fluid exit port are disposed in the top of the fluid separation vessel.

10. The system of claim 9, wherein the purging fluid comprises compressed gas, the purging fluid exit line comprises a vent.

11. The system of claim 9, wherein the purging fluid comprises a liquid; and the purging fluid exit line connectively links the purging fluid exit port to the second sample fluid disposal line.

12. The system of claim 8, further comprising:
a first purging fluid source comprising a first purging fluid and a second purging fluid source comprising a second purging fluid, where the first purging fluid source is operatively linked to a first pump, the second purging fluid source is operatively linked to a second pump, and where each of the first and second purging fluids is a liquid;
a first purging fluid intake line connectively linking the first purging fluid source to the fluid separation vessel via a first purging fluid entry port disposed in the top of the fluid separation vessel;
a second purging fluid intake line connectively linking the second purging fluid source to the fluid separation vessel via a second purging fluid entry port disposed in the bottom of the fluid separation vessel;
a sample fluid exit line connectively linking a sample fluid exit port disposed in a side portion of the fluid separation vessel to the first sample fluid disposal line or a plurality of collection vessel intake lines, where each collection vessel intake line is connectively linked to a collection vessel; and
a purging fluid exit line connectively linking the a purging fluid exit port disposed in the top of the fluid separation vessel to a sample fluid disposal line,
wherein the first purging fluid entry port is positioned for receiving the first purging fluid from the first purging fluid source so as to drive out at least a portion of the aqueous phase fluid fraction through the sample fluid exit port;
wherein the second purging fluid entry port is positioned for receiving the second purging fluid from the second purging fluid source so as to drive out fluids remaining on the other side of the plunger through the first purging fluid exit port following removal of the portion of the aqueous phase fluid fraction; and
wherein each of the first and second purging fluid intake lines, the sample fluid exit line, and the purging fluid exit line comprises a solenoid valve operatively linked to the controller for managing flow of sample fluids therethrough in a predetermined manner.

13. The system of claim 12, further comprising a second purging fluid exit line connectively linking the second purging fluid source to the fluid separation vessel via a second purging fluid exit port disposed in the bottom of the fluid separation vessel,
wherein the second purging fluid exit line is configured for recycling the second purging fluid back into the second purging fluid source as the sample fluids are drawn into the fluid separation vessel through the sample fluid entry port.

14. The system of claim 12, wherein the sample fluid entry port and the first purging fluid entry port are commonly shared and the sample fluid intake line and the first purging fluid intake line are joined upstream of the commonly shared entry port forming a joint sample fluid/purging fluid intake line through which sample fluids from the sample fluid source and the first purging fluid source are supplied to the fluid separation vessel.

15. The system of claim 12, wherein the first purging fluid source comprises a gas; and the second purging fluid source comprises a liquid.

16. The system of claim 12, wherein each of the first and second purging fluid sources comprises a gas.

17. The system of claim 6, where the pluralities of inlet ports, outlet ports, and fluid lines are operatively positioned for collecting a gas phase fluid fraction in a sample fluid collection vessel.

18. The system of claim 17, wherein:
the sample fluid intake line connectively links the pressurized line to a sample fluid entry port disposed in the top of the fluid separation vessel;
the purging fluid intake line connectively links the purging fluid source to a purging fluid entry port disposed in the bottom of the fluid separation vessel;

a sample fluid exit line connectively links a sample fluid exit port disposed in the top or side of the fluid separation vessel to the first sample fluid disposal line and the plurality of collection vessel intake lines;

a first purging fluid exit line connectively links a purging fluid exit port disposed in the bottom of the fluid separation vessel to the purging fluid source; and a second purging fluid exit line connectively links a second purging fluid exit port disposed in the bottom of the fluid separation vessel to the sample fluid exit line.

19. The system of claim 18, wherein a liquid catch can for dehydrating gas phase fluids flowing therethrough is operatively linked to the sample fluid exit line between a proximal solenoid valve in the sample fluid exit line and a branchpoint in the sample fluid exit line linking the sample fluid exit line to the first sample fluid disposal line.

20. The system of claim 18, wherein the purging fluid source comprises a liquid and the purging fluid exit line connectively links a purging fluid exit port disposed in the bottom of the fluid separation vessel to the purging fluid source so that the purging fluid can be recycled back to the purging fluid source as the sample fluids are received in the fluid separation vessel from the sample fluid source through the sample fluid entry port.

21. The system of claim 18, wherein the purging fluid source comprises compressed gas and the purging fluid exit line extends from the purging fluid exit port, and wherein the purging fluid exit line comprises a vent positioned so that the gas can be released into the atmosphere as the sample fluids are received into the fluid separation vessel from the sample fluid source through the sample fluid entry port.

22. The system of claim 6, wherein the pluralities of inlet ports, outlet ports, and fluid lines are operatively positioned for collecting an organic phase fluid fraction in a sample fluid collection vessel.

23. The system of claim 22, wherein:

the sample fluid intake line connectively links the pressurized line to a sample fluid entry port disposed in the top of the fluid separation vessel;

the purging fluid intake line connectively links the purging fluid source to a purging fluid entry port disposed in the bottom of the fluid separation vessel;

a first purging fluid exit line connectively links a purging fluid exit port disposed in the bottom of the fluid separation vessel to the purging fluid source;

a second purging fluid exit line connectively links a second purging fluid exit port disposed in the bottom of the fluid separation vessel to the sample fluid exit line;

a sample fluid exit line connectively links a sample fluid exit port disposed in the top of the fluid separation vessel to the first sample fluid disposal line and each of the plurality of collection vessel intake lines;

the first sample fluid disposal line extends from a second branchpoint in the sample fluid exit line to a second fluid disposal line and the second sample fluid disposal line connectively links the disposal vessel to the first sample fluid disposal line and each of the plurality of collection vessel exit lines; and each of the sample fluid intake line, the purging fluid intake line, the first and second purging fluid exit lines, the sample fluid exit line, the first sample fluid disposal line, and each of the plurality of the collection vessel intake lines and collection vessel exit lines comprises a solenoid valve controlling flow of fluids therethrough.

24. The system of claim 23, wherein the sample fluid exit line comprises:

a capillary viscometer proximal to the first branchpoint, the viscometer capable of measuring the pressure differential of sample fluids flowing therethrough so that the gas phase fluid fraction can be diverted to the disposal vessel via the first sample fluid disposal line prior to collection of the organic phase fluid fraction.

25. A method for obtaining sample fluids from a sample fluid source:

(a) providing an automated fluid sampling system comprising:

(1) a pressurized line operatively linked to a sample fluid source comprising sample fluids;

(2) a fluid separation vessel operatively linked to the pressurized line by a sample fluid intake line, the fluid separation vessel comprising a plunger for collecting sample fluids therein and purging fluids therefrom, the fluid separation vessel further comprising a plurality of inlet ports and a plurality of outlet ports disposed in top, bottom or side portions of the fluid separation vessel for mediating flow of fluids therethrough;

(3) a sample fluid collection vessel operatively linked to the fluid separation vessel;

(4) a purging fluid source operatively linked to the fluid separation vessel, the purging fluid source comprising a purging fluid;

(5) a disposal vessel for receiving fluids purged from the fluid separation vessel;

(6) a plurality of fluid lines operatively linking the fluid separation vessel to the pressurized line, the purging fluid source, the sample fluid collection vessel, and the disposal vessel;

(7) solenoid valves operatively linked to each of the plurality of fluid lines in (6); and (8) a controller selectively controlling fluid flow though each of the plurality of fluid lines in a predetermined manner;

(b) filling the fluid separation vessel with sample fluids from the sample fluid source via the pressurized line;

(c) allowing a sufficient period of time for gravity-mediated phase separation of the sample fluids into at least two phase separated fluid fractions; and (d) collecting a selected phase separated fluid fraction in a sample fluid collection vessel.

26. The method of claim 25, wherein the system in step (a) comprises pluralities of sample fluid collection vessels, collection vessel intake lines, and collection vessel exit lines, where the method comprises repeating steps (b)-(d) to collect a phase separated fluid fraction in each of the plurality of sample fluid collection vessels, and wherein collection of at least one phase separated fluid fraction into a sample fluid collection vessel is time-dependent.

27. The method of claim 26, wherein the plurality of sample fluid collection vessels are housed as an array in a sample box.

28. The method of claim 25, wherein the step of collecting the phase separated fluid fraction in a collection vessel is coincident with introduction of a purging fluid into the fluid separation vessel.

29. The method of claim 25, wherein the step of collecting the phase separated fluid fraction in a collection vessel comprises introducing a purging fluid into the fluid separation vessel so as to vertically displace the plunger and fluids contained on the opposite side of the plunger.

30. The method of claim 25, wherein the step of collecting the phase separated fluid fraction in a collection vessel comprises introducing a purging fluid directly behind sample fluids on the same side of the plunger so as to drive a phase separated fluid fraction out of the fluid separation vessel toward a sample fluid collection vessel.

31. The method of claim 25, wherein the step of collecting the phase separated fluid fraction in a collection vessel comprises introducing a purging fluid into the fluid separation vessel so as to displace the plunger in the fluid separation vessel and drive a phase separated fluid fraction on the other side of the plunger out of the fluid separation vessel toward a sample fluid collection vessel.

32. The method of claim 25, wherein the step of collecting the phase separated fluid fraction in a collection vessel is coincident with removal of a purging fluid within the fluid separation vessel.

33. The method of claim 25, further comprising the step of introducing a purging fluid through the fluid separation vessel to flush out a fluid line downstream of the fluid separation vessel.

34. The method of claim 25, further comprising the step of recycling a purging fluid from the fluid separation vessel back to its corresponding purging fluid source.

35. The method of claim 25, wherein the system in step (a) is operatively linked to a production well or injection well.

36. The method of claim 25, wherein the system in step (a) comprises a filtration system between the pressurized line and the fluid separation vessel, the filtration system being configured to remove solids, salts, and other formations received from the pressurized line.

37. The method of claim 25, wherein the system in step (a) comprising a sample fluid intake line, a sample fluid exit line, a first sample fluid disposal line, a second sample fluid disposal line, a purging fluid intake line, and a purging fluid exit line, wherein:
  the sample fluid intake line operatively links the pressurized line to the fluid separation vessel;
  the sample fluid exit line operatively links the fluid separation vessel to a first sample fluid disposal line and a plurality of collection vessel intake lines,
  the first sample fluid disposal line operatively links the disposal vessel or the second sample fluid disposal line to the sample fluid exit line,
  each collection vessel intake line is operatively linked to a collection vessel, where the sample fluid exit line comprises proximal and distal solenoid valves controlling flow of fluids therethrough, including a branchpoint between the proximal and distal solenoid valves connectively linking the sample fluid exit line and the first sample fluid disposal line;
  the second sample fluid disposal line operatively links the disposal vessel to the first sample fluid disposal line and the plurality of collection vessel exit lines, where each collection vessel exit line is connectively linked to a collection vessel;
  the purging fluid intake line operatively links the purging fluid source to the fluid separation vessel;
  the purging fluid exit line operatively links the fluid separation vessel to the second sample fluid disposal line or a vent to the atmosphere;
  each of the sample fluid intake line, the sample fluid exit line, the plurality of collection vessel intake lines, the plurality of collection vessel exit lines, the purging fluid intake line, the purging fluid exit line, and the first sample fluid disposal line comprises a solenoid valve controlling flow of fluids therethrough, and
  the controller is configured to open or close each solenoid valve in each one of the sample fluid intake line, the sample fluid exit line, the plurality of collection vessel intake lines, the plurality of collection vessel exit lines, the purging fluid intake line, the purging fluid exit line, and the first sample fluid disposal line in a predetermined manner.

38. The method of claim 37, wherein the predetermined manner by which the solenoid valves are opened or closed is dependent on time, sample fluid source, fluid pressure, fluid flow rate or a combination thereof.

39. The method of claim 38, wherein the fluid separation vessel in the system in step (a) comprises:
  a sample fluid entry port positioned for receiving sample fluids from the pressurized line;
  a sample fluid exit port positioned for removing phase separated fluid fractions from the fluid separation vessel via the sample fluid exit line;
  a purging fluid entry port positioned for receiving a purging fluid from the purging fluid source via the purging fluid intake line to facilitate collection of the phase separated fluid fraction, purging of sample fluids remaining in the fluid separation vessel following collection of the phase separated fluid fraction, or both;
  a purging fluid exit port positioned for removing a purging fluid or sample fluids remaining in the fluid separation vessel following removal of the phase separated fluid fraction from the fluid separation vessel via the purging fluid exit line and collection of the phase separated fluid fraction into the collection vessel.

40. The method of claim 39, wherein the fluid separation vessel in the system in step (a) comprises pluralities of inlet ports, outlet ports, and fluid lines operatively positioned for collecting an aqueous phase fluid fraction in a sample fluid collection vessel.

41. The method of claim 40, wherein the system in step (a) comprises a plurality of collection vessels, wherein:
  each collection vessel is operatively linked to a collection vessel intake line and a collection vessel exit line;
  each collection vessel intake line is operatively linked to the sample fluid exit line; and
  each collection vessel exit line is operatively linked to a second sample fluid disposal line.

42. The method of claim 41, wherein the system in step (a) further comprises a fluid separation vessel wherein:
  the sample fluid entry port and the sample fluid exit port are disposed in the bottom of the fluid separation vessel, and
  the purging fluid entry port and the purging fluid exit port are disposed in the top of the fluid separation vessel.

43. The method of claim 42, wherein the filling the fluid separation vessel with the sample fluids comprises the steps of:
  closing the purging fluid intake line and the sample fluid exit line so that flow of fluids is restricted therethrough; and
  opening the sample fluid intake line and the purging fluid exit line so that the sample fluids from the sample fluid source flow through the sample fluid intake line and into the fluid separation vessel, driving fluids on the opposite side of the plunger to flow out of the fluid separation vessel, through the purging fluid exit line.

44. The method of claim 42, wherein the collecting the aqueous phase fluid fraction in a collection vessel comprises the steps of:

closing the sample fluid intake line, the purging fluid exit line, and the first sample fluid disposal line so that flow of fluids is restricted therethrough, opening the purging fluid intake line; and opening the distal solenoid valve in the sample fluid exit line and a selected collection vessel intake line.

45. The method of claim 41, wherein the system in step (a) comprises a first purging fluid source comprising a first purging fluid and a second purging fluid comprising a second purging fluid, wherein the first purging fluid source is operatively linked to a first pump, the second purging fluid source is operatively linked to a second pump, and each of the first and second purging fluids is a liquid, wherein the system in step (a) further comprises a first purging fluid intake line, a second purging fluid intake line, and a fluid separation vessel, wherein:

the top of the fluid separation vessel comprises the sample fluid entry port, a first purging fluid entry port and a first purging fluid exit port;

the bottom of the fluid separation vessel comprises a second purging fluid entry port;

a side portion of the fluid separation vessel comprises the sample fluid exit port; and the fluid separation vessel receives a first purging fluid from the first purging fluid source through the first purging fluid entry port, the fluid separation vessel receives the second purging fluid from the second purging fluid source through the second purging fluid entry port;

the first purging fluid entry port is operatively linked to the first purging fluid intake line; and the second purging fluid entry port is operatively linked to the second purging fluid intake line.

46. The method of claim 44, wherein the first purging fluid comprises a gas and the second purging fluid comprises a liquid.

47. The method of claim 44, wherein the sample fluid entry port and the first purging fluid entry port are the same.

48. The method of claim 47, wherein filling the fluid separation vessel with sample fluids comprises the steps of:

closing each of the first purging fluid intake line, the first purging fluid exit line, the second purging fluid intake line, and the distal solenoid valve in the sample fluid exit line so that flow of fluids is restricted therethrough; and opening the sample fluid intake line, the sample fluid exit line, and the first sample fluid disposal line so that the sample fluids from the sample fluid source flow through the sample fluid entry port into the fluid separation vessel and so the second purging fluid flows out of the fluid separation vessel, through the sample fluid exit line, through the first sample fluid disposal line, and into the disposal vessel.

49. The method of claim 47, wherein collecting the aqueous phase fluid fraction in a collection vessel comprises the steps of:

closing the sample fluid intake line, the purging fluid exit line, the second purging fluid intake line, and the first sample fluid disposal line so that flow of fluids is restricted therethrough; and opening the first purging fluid intake line, the proximal and distal solenoid valves in the sample fluid exit line, and a collection vessel intake line so that the sample fluids flow into the sample fluid collection vessel.

50. The method of claim 47, wherein purging the fluid separation vessel of fluids following collection of the aqueous phase fluid fraction comprises the steps of:

closing the sample fluid intake line, the first purging fluid intake line, and the sample fluid exit line; and opening the second purging fluid intake line and the first purging fluid exit line so that sample fluids and first purging fluid remaining in the fluid separation vessel above the plunger flow out of the fluid separation vessel, through the first purging fluid exit line, through the first sample fluid disposal line and into the second fluid disposal line or the disposal vessel.

51. The method of claim 45, wherein the system in step (a) includes a second purging fluid exit line operatively linking a second purging fluid exit port disposed in the bottom of the fluid separation vessel to the second purging fluid source.

52. The method of claim 51, wherein filling the fluid separation vessel with sample fluids and recycling the second purging fluid comprise the steps of:

closing each of the first purging fluid intake line, the second purging fluid intake line, the first purging fluid exit line, and the proximal solenoid valve in the sample fluid exit line; and opening the sample fluid intake line and the second purging fluid exit line so that the sample fluids from the sample fluid source flow through the sample fluid entry port into the fluid separation vessel, driving the second purging fluid on the other side of the plunger out of fluid separation vessel and into the second purging fluid source.

53. The method of claim 39, wherein the fluid separation vessel in the system in step (a) comprises pluralities of inlet ports, outlet ports, and fluid lines operatively positioned for collecting a gas phase fluid fraction in a sample fluid collection vessel.

54. The method of claim 53, wherein the system in step (a) comprises:

a sample fluid intake line connectively linking the pressurized line to a sample fluid entry port disposed in the top of the fluid separation vessel;

a purging fluid intake line connectively linking the purging fluid source to a purging fluid entry port disposed in the bottom of the fluid separation vessel;

a sample fluid exit line connectively linking a sample fluid exit port disposed in the top or side of the fluid separation vessel to the first sample fluid disposal line and a plurality of collection vessel intake lines;

a first purging fluid exit line connectively linking a purging fluid exit port disposed in the bottom of the fluid separation vessel to the purging fluid source; and a second purging fluid exit line connectively linking a second purging fluid exit port disposed in the bottom of the fluid separation vessel to the sample fluid exit line.

55. The method of claim 54, wherein the system in step (a) comprises a liquid catch can operatively linked to the sample fluid exit line downstream of the proximal solenoid valve in the sample fluid exit line and upstream of the branchpoint in the sample fluid exit line, and wherein the liquid catch can is configured for dehydrating gas phase fluids flowing therethrough.

56. The method of claim 54, wherein filling the fluid separation vessel with sample fluids and recycling the purging fluid back to the purging fluid source comprise the steps of:

closing the proximal solenoid valve in the sample fluid exit line, the purging fluid intake line, and the second purging fluid exit line so that flow of fluids is restricted therethrough; and opening the sample fluid intake line and the first purging fluid exit line so that the sample fluids from the sample fluid source flow through the sample fluid entry port into the fluid separation vessel, driving the purging fluid on the other side of the plunger out of fluid separation vessel and into the purging fluid source.

57. The method of claim 54, wherein filling the fluid separation vessel with sample fluids and flushing the sample fluid exit line with the purging fluid comprise the steps of:
closing the proximal and distal solenoid valves in the sample fluid exit line, the purging fluid intake line, and the first purging fluid exit line so that flow of fluids is restricted therethrough; and
opening the sample fluid intake line, the second purging fluid exit line, and the first sample fluid disposal line so that as the sample fluids from the sample fluid source flow through the sample fluid entry port into the fluid separation vessel, the purging fluid on the other side of the plunger is driven out of fluid separation vessel, through the second purging fluid exit line, into the sample fluid exit line, through the first sample fluid disposal line and into the disposal vessel, flushing the sample fluid exit line with the purging fluid.

58. The method of claim 54, wherein collecting the gas phase fluid fraction in a collection vessel comprises the steps of:
closing the sample fluid intake line, the purging fluid exit line, the purging fluid exit line, and the second solenoid valve in the sample fluid exit line so that flow of fluids is restricted therethrough; and
opening the sample fluid exit line, a collection vessel intake line, and the purging fluid intake line so that as the purging fluid from the purging fluid source flows up through the purging fluid entry port into the fluid separation vessel, at least a portion of the gas phase fluid fraction on the other side of the plunger is driven up and out of the fluid separation vessel, into a sample fluid collection vessel.

59. The method of claim 54, wherein purging fluids remaining in the fluid separation vessel following collection of the gas phase fluid fraction comprises the steps of:
closing the distal solenoid valve in the sample fluid exit line after the gas phase fluid fraction has been collected; and
opening the first sample fluid disposal line so that the sample fluids remaining above the plunger flow out of the fluid separation vessel through the sample fluid exit port toward the disposal vessel.

60. The method of claim 39, wherein the fluid separation vessel in the system in step (a) comprises pluralities of inlet ports, outlet ports, and fluid lines operatively positioned for collecting an organic phase fluid fraction in a sample fluid collection vessel.

61. The method of claim 60, wherein the system in step (a) comprises:
a sample fluid intake line connectively linking the pressurized line to a sample fluid entry port disposed in the top of the fluid separation vessel;
a purging fluid intake line connectively links the purging fluid source to a purging fluid entry port disposed in the bottom of the fluid separation vessel;
a first purging fluid exit line connectively links a purging fluid exit port disposed in the bottom of the fluid separation vessel to the purging fluid source;
a second purging fluid exit line connectively links a second purging fluid exit port disposed in the bottom of the fluid separation vessel to the sample fluid exit line at a first branchpoint;
a sample fluid exit line connectively links a sample fluid exit port disposed in the top of the fluid separation vessel to the first sample fluid disposal line and each of the plurality of collection vessel intake lines;
the first sample fluid disposal line extends from second branchpoint in the sample fluid exit line to a second fluid disposal line;
the second sample fluid disposal line connectively links the disposal vessel to the first sample fluid disposal line and each of the plurality of collection vessel exit lines; and
each of the sample fluid intake line, the purging fluid intake line, the first and second purging fluid exit lines, the sample fluid exit line, the first sample fluid disposal line, and each of the plurality of collection vessel intake lines and collection vessel exit lines comprises a solenoid valve controlling flow of fluids therethrough.

62. The method of claim 61, wherein a capillary viscometer is operatively linked to the sample fluid exit line between its proximal solenoid valve and the second branchpoint in the sample fluid exit line, and
wherein the capillary viscometer is configured for measuring the pressure differential of sample fluids flowing therethrough,
a capillary viscometer proximal to the branchpoint, the viscometer capable of measuring the pressure differential of sample fluids flowing therethrough so that the gas phase fluid fraction can be diverted to the disposal vessel via the first sample fluid disposal line prior to collection of the organic phase fluid fraction, and
a second solenoid valve downstream of the first disposal line, proximal to a collection vessel intake line.

63. The method of claim 61, wherein filling the fluid separation vessel with sample fluids and recycling the purging fluid back to the purging fluid source comprise the steps of:
closing the proximal solenoid valve in the sample fluid exit line, the purging fluid intake line, and the second purging fluid exit line so that flow of fluids is restricted therethrough; and
opening the sample fluid intake line and the first purging fluid exit line so that the sample fluids from the sample fluid source flow through the sample fluid entry port into the fluid separation vessel, driving the purging fluid on the other side of the plunger out of fluid separation vessel and into the purging fluid source.

64. The method of claim 61, wherein filling the fluid separation vessel with sample fluids and flushing the sample fluid exit line with the purging fluid comprise the steps of:
closing the proximal and distal solenoid valves in the sample fluid exit line, the purging fluid intake line, and the first purging fluid exit line so that flow of fluids is restricted therethrough; and
opening the sample fluid intake line, the second purging fluid exit line, and the first sample fluid disposal line so that as the sample fluids from the sample fluid source flow through the sample fluid entry port into the fluid separation vessel, the purging fluid on the other side of the plunger is driven down and out of fluid separation vessel, through the second purging fluid exit line, into the sample fluid exit line, through the first sample fluid disposal line and into the disposal vessel, flushing the sample fluid exit line with the purging fluid.

65. The method of claim 61, wherein collecting the organic phase fluid fraction in a collection vessel comprise the steps of:
  closing the sample fluid intake line, the first purging fluid exit line, the second purging fluid exit line, and the distal solenoid valve in the sample fluid exit line so that flow of fluids is restricted therethrough;
  opening the purging fluid intake line, the proximal solenoid valve in the sample fluid exit line, and the first sample fluid disposal line so that as the purging fluid from the purging fluid source flows up through the purging fluid entry port into the fluid separation vessel, the gas phase fluid fraction on the other side of the plunger is driven up and out of the fluid separation vessel, through the first sample fluid disposal line and into the disposal vessel;
  following removal of gas through the first sample fluid disposal line, closing the first sample fluid disposal line, opening the distal solenoid valve in the sample fluid exit line, and opening a collection vessel intake line so that at least a portion of the organic phase fluid fraction is collected in a collection vessel.

66. The method of claim 61, wherein purging fluids remaining in the fluid separation vessel following collection of the organic phase fluid fraction comprises the steps of:
  closing the distal solenoid valve in the sample fluid exit line and the collection vessel intake lines after the organic phase fluid fraction has been collected; and
  opening the first sample fluid disposal line so that the sample fluids remaining above the plunger flow out of the fluid separation vessel through the sample fluid exit port toward the disposal vessel.

67. The method of claim 39, wherein the system in step (a) is located in an oil well field and the method further comprises the step of introducing a tracer into an injection well or production well located in the oil well field.

68. The method of claim 67, further comprising the step of introducing tracers in a plurality of injection wells, production wells, or a combination thereof, wherein the injection wells and production wells are located in the oil well field.

69. The method of claim 39, wherein the system in step (a) is located in a gas well field and the method further comprises the step of introducing a tracer into an injection well or production well located in the gas well field.

70. The method of claim 69, further comprising the step of introducing tracers in a plurality of injection wells, production wells, or a combination thereof, wherein the injection wells and production wells are located in the gas well field.

71. A method for assembling an automated fluid sampling system, the method comprising the steps of operatively linking:
  (a) a pressurized line to a plunger equipped fluid separation vessel by a sample fluid intake line, the pressurized line being operatively linked to a sample fluid source comprising sample fluids;
  (b) the plunger equipped fluid separation vessel to a sample fluid exit line, a purging fluid intake line, and a purging fluid exit line;
  (c) the sample fluid exit line to a first sample fluid disposal line and a plurality of collection vessel intake lines;
  (d) a second sample fluid disposal line to a disposal vessel;
  (e) the first sample fluid disposal line to a disposal vessel or the second sample fluid disposal line;
  (f) each of the plurality collection vessel intake lines to a collection vessel;
  (g) each of the collection vessels to one of a plurality of collection vessel exit lines;
  (h) each of the plurality of collection vessel exit lines to the second sample fluid disposal line;
  (i) a solenoid valve to each of the sample fluid intake line, the sample fluid exit line, the first sample fluid disposal line, the purging fluid intake line, the purging fluid exit line, and each of the pluralities of collection vessel intake lines and collection vessel exit lines, each solenoid valve being configured to selectively control fluid flow therethrough; and
  (j) a controller to the solenoid valves so that each of the solenoid valves can be selectively opened or closed in a predetermined manner.

\* \* \* \* \*